(12) United States Patent
Howarth et al.

(10) Patent No.: US 12,275,762 B2
(45) Date of Patent: Apr. 15, 2025

(54) POLYPEPTIDE AND ITS USE IN AFFINITY PURIFICATION

(71) Applicant: Oxford University Innovation Limited, Oxford (GB)

(72) Inventors: Mark Howarth, Oxford (GB); Irsyad Khairil Anuar, Oxford (GB)

(73) Assignee: OXFORD UNIVERSITY INNOVATION LIMITED, Oxford (GB)

( * ) Notice: Subject to any disclaimer, the term of this patent is extended or adjusted under 35 U.S.C. 154(b) by 973 days.

(21) Appl. No.: 17/299,849

(22) PCT Filed: Dec. 5, 2019

(86) PCT No.: PCT/EP2019/083905
§ 371 (c)(1),
(2) Date: Jun. 4, 2021

(87) PCT Pub. No.: WO2020/115252
PCT Pub. Date: Jun. 11, 2020

(65) Prior Publication Data
US 2022/0041663 A1    Feb. 10, 2022

(30) Foreign Application Priority Data

Dec. 5, 2018  (GB) .................................. 1819850.7

(51) Int. Cl.
*C07K 14/315*  (2006.01)
*C07K 1/14*  (2006.01)

(52) U.S. Cl.
CPC .............. *C07K 14/315* (2013.01); *C07K 1/14* (2013.01)

(58) Field of Classification Search
CPC ................................ C07K 14/315; C07K 1/14
See application file for complete search history.

(56) References Cited

FOREIGN PATENT DOCUMENTS

| WO | 2011/098772 A1 | 8/2011 |
| WO | 2014/176311 A1 | 10/2014 |
| WO | 2016/112921 A1 | 7/2016 |
| WO | 2016/193746 A1 | 12/2016 |
| WO | 2018/189517 A1 | 10/2018 |
| WO | 2018/197854 A1 | 11/2018 |

OTHER PUBLICATIONS

Sumper et al. (Primary structure and glycosylation of the S-layer protein of Haloferax volcanii. J. Bacteriol. (1990), 172(12): 7111-7118) (Year: 1990).*
International Search Report and Written Opinion for WO 2020/115252 (PCT/EP2019/083905), dated Feb. 12, 2020, pp. 1-16.
JK Search Report for GB 1819850.7, dated May 20, 2019, pp. 1-5.
B. Zakeri et al: "Peptide tag forming a rapid covalent bond to a protein, through engineering a bacterial adhesin", Proceedings of the National Academy of Sciences, vol. 109, No. 12, Mar. 20, 2012 (Mar. 20, 2012), pp. E690-E697.
Keeble A H et al: "Evolving accelerated amidation by SpyTag/SpyCatcher to analyze membrane dynamics", Angew. Chem. Int. Ed., vol. 56, Dec. 1, 2017 (Dec. 1, 2017), pp. 16521-16525.
Xia-Ling Wu et al: "An Intrinsically Disordered Peptide-Peptide Stapler for Highly Efficient Protein Ligation Both in Vivo and in Vitro", Journal of the American Chemical Society, vol. 140, No. 50, Nov. 19, 2018 (Nov. 19, 2018), pp. 17474-17483.
Li Long et al: "Structural Analysis and Optimization of the Covalent Association between SpyCatcher and a Peptide Tag", Journal of Molecular Biology, Academic Press, United Kingdom, vol. 426, No. 2, Oct. 23, 2013 (Oct. 23, 2013), pp. 309-317.
Xinyu Zhao et al: "Several Affinity Tags Commonly Used in Chromatographic Purification", Journal of Analytical Methods in Chemistry, vol. 2013, Jan. 1, 2013 (Jan. 1, 2013), pp. 1-8.
I Rsyad N. A. Khairi L Anuar et al: "Spy&Go purification of SpyTag-proteins using pseudo-SpyCatcher to access an oligomerization toolbox", Nature Communications, vol. 10, No. 1. Apr. 15, 2019 (Apr. 15, 2019), p. 1734.
Curr Opin Chem Biol, vol. 29, Dec. 2015, Reddington & Howarth, "Secrets of a covalent interaction for biomaterials and biotechnology: SpyTag and SpyCatcher", pp. 94-99.
Alves NJ et al, J Vis Exp. Nov. 16, 2016;(117), "Directed Protein Packaging within Outer Membrane Vesicles from *Escherichia coli*: Design, Production and Purification."
Alves NJ et al, Sci Rep. Apr. 27, 2016;6:24866, "Protecting enzymatic function through directed packaging into bacterial outer membrane vesicles."

(Continued)

*Primary Examiner* — Iqbal H Chowdhury
(74) *Attorney, Agent, or Firm* — Thomas|Horstemeyer, LLP

(57) ABSTRACT

The present invention relates to an affinity purification system that utilises a polypeptide comprising: (i) an amino acid sequence as set forth in SEQ ID NO: 1, wherein X at position 79 is selected from alanine, glycine, serine, asparagine, or threonine; (ii) a portion of (i) comprising an amino acid sequence as set forth in SEQ ID NO: 2, wherein X at position 56 is selected from alanine, glycine, serine, asparagine or threonine; (iii) an amino acid sequence with at least 80% sequence identity to a sequence as set forth in SEQ ID NO: 1, wherein the polypeptide comprises alanine, glycine, serine, asparagine or threonine at a position equivalent to position 79 of SEQ ID NO: 1; or (iv) a portion of (iii) comprising an amino acid sequence with at least 80% sequence identity to a sequence as set forth in SEQ ID NO: 2, wherein the polypeptide comprises alanine, glycine, serine, asparagine or threonine at a position equivalent to position 56 of SEQ ID NO: 2, wherein the polypeptide binds selectively and reversibly to a peptide comprising an amino acid sequence as set forth in SEQ ID NO: 3, 4 or 5.

12 Claims, 13 Drawing Sheets
Specification includes a Sequence Listing.

(56) References Cited

OTHER PUBLICATIONS

Alves NJ et al, ACS Appl Mater Interfaces. Nov. 11, 2015;7(44):24963-72, "Bacterial Nanobioreactors—Directing Enzyme Packaging into Bacterial Outer Membrane Vesicles."
Bedbrook CN et al, Chem Biol. Aug. 20, 2015;22(8):1108-21, "Genetically Encoded Spy Peptide Fusion System to Detect Plasma Membrane-Localized Proteins in vivo."
Botyanszki et al., 2015, Biotechnology and bioengineering 112, 2016-2024, "Engineered Catalytic Biofilms: Site-Specific Enzyme Immobilization onto E. coli Curli Nanofibers."
Brune et al., 2016, Scientific reports 6, 19234, "Plug-and-Display: decoration of Virus-Like Particles via isopeptide bonds for modular immunization."
Brune et al. 2017, Bioconjugate Chem. 28, 1544-1551, "Dual Plug-and-Display Synthetic Assembly Using Orthogonal Reactive Proteins for Twin Antigen Immunization."
Chen et al., 2011, Proc Natl Acad Sci U S A 108, 11399-11404, "A general strategy for the evolution of bond-forming enzymes using yeast display."
Chen AY et al, Nat Mater. May 2014;13(5):515-23, "Synthesis and patterning of tunable multiscale materials with engineered cells."
Dorval Courchesne et al, ACS Biomater. Sci. Eng. 2017, 3, 5, 733-741, "Scalable Production of Genetically Engineered Nanofibrous Macroscopic Materials via Filtration."
Dovala D et al, Protein Expr Purif. Jan. 2016;117:44-51, "Rapid analysis of protein expression and solubility with the SpyTag-SpyCatcher system."
Fairhead M et al, Journal of the American Chemical Society Sep. 3, 2014;136(35):12355-63, "SpyAvidin Hubs Enable Precise and Ultrastable Orthogonal Nanoassembly."
Fierer JO et al, Proc Natl Acad Sci U S A. Apr. 1, 2014;111(13):E1176-81, "SpyLigase peptide—peptide ligation polymerizes affibodies to enhance magnetic cancer cell capture."
Fuller CW et al, Proc Natl Acad Sci U S A. May 10, 2016;113(19):5233-8, "Real-time single-molecule electronic DNA sequencing by synthesis using polymer-tagged nucleotides on a nanopore array."
Gao X et al, Biomacromolecules. Sep. 12, 2016;17(9):2812-9, "Engineering Protein Hydrogels Using SpyCatcher-SpyTag Chemistry.".
Giessen TW, Silver P., Chembiochem. Oct. 17, 2016;17(20):1931-1935, "A Catalytic Nanoreactor Based on in Vivo Encapsulation of Multiple Enzymes in an Engineered Protein Nanocompartment."
Gilbert et al, ACS Synth. Biol. 2017, 6, 6, 957-967, "Extracellular Self-Assembly of Functional and Tunable Protein Conjugates from Bacillus subtilis."
I.N.A. Khairil Anuar, Nov. 4-7, 2018: "Spy&Go: purifying SpyTag-proteins using pseudo-SpyCatcher for downstream bioconjugation reactions. Presentation slides", The 38th International Symposium on the Purification of Proteins, Peptides, and Polynucleotides (ISPPP 2018).
Jaffe et al., 1996, Molecular Microbiology 21, 373-384, "Protein F2, a novel fibronectin-binding protein from *Streptococcus pyogenes*, possesses two binding domains."
Janitzek CM et al, Malar J. Nov. 8, 2016;15(1):545, "Bacterial superglue generates a full-length circumsporozoite protein virus-like particle vaccine capable of inducing high and durable antibody responses."
Khairil Anuar and M. Howarth, Nov. 4-7, 2018: Bacterial superglue engineered for protein separation and plug-and-display nanoassembly. Abstract; The 38th International Symposium on the Purification of Proteins, Peptides, and Polynucleotides (ISPPP 2018).
Lakshmanan A et al, ACS Nano. Aug. 23, 2016;10(8):7314-22, "Molecular Engineering of Acoustic Protein Nanostructures."
Leonard JD, Narlikar GJ., Mol Cell. Mar. 5, 2015;57(5):850-9, "A Nucleotide-Driven Switch Regulates DNA Length Sensing by a Dimeric Chromatin Remodeler."
Liu X et al, Sci Rep. Nov. 29, 2016;6:38019, "Engineering Genetically-Encoded Mineralization and Magnetism via Directed Evolution."
Liu Z et al, Oncoimmunology. Mar. 10, 2016;5(6):e1147641, "A novel dendritic cell targeting HPV16 E7 synthetic vaccine in combination with PD-L1 blockade elicits therapeutic antitumor immunity in mice."
Liu Z et al, Sci Rep. Dec. 1, 2014;4:7266, "A novel method for synthetic vaccine construction based on protein assembly."
Min D et al, Protein Sci. Aug. 2016;25(8):1535-44, "A simple DNA handle attachment method for single molecule mechanical manipulation experiments."
Moon et al, Chem Commun (Camb). Nov. 29, 2016;52(97):14051-14054, "Plug-and-Playable Fluorescent Cell Imaging Modular Toolkits Using the Bacterial Superglue, SpyTag/SpyCatcher."
Nguyen PQ et al, Nat Commun. Sep. 17, 2014;5:4945, "Programmable biofilm-based materials from engineered curli nanofibres."
Pardee K et al, Cell. Sep. 22, 2016;167(1):248-259, "Portable, On-Demand Biomolecular Manufacturing."
Schloss et al, ACS Biomater. Sci. Eng. 2016, 2, 11, 1856-1861, "Fabrication of Modularly Functionalizable Microcapsules Using Protein-Based Technologies."
Schmid-Burgk et al, Nat Commun. Jul. 28, 2016;7:12338, "CRISPaint allows modular base-specific gene tagging using a ligase-4-dependent mechanism."
Schoene C et al, Angewandte Chemie. Jun. 10, 2014;53(24):6101-4, "SpyTag/SpyCatcher Cyclization Confers Resilience to Boiling on a Mesophilic Enzyme."
Schoene et al., 2016, Scientific reports 6, 21151, "SpyRing interrogation: analyzing how enzyme resilience can be achieved with phytase and distinct cyclization chemistries."
Si M et al, PLoS One. Sep. 22, 2016;11(9):e0162318, "SpyTag/SpyCatcher Cyclization Enhances the Thermostability of Firefly Luciferase."
Siegmund et al, Sci Rep. Dec. 16, 2016;6:39291, "Spontaneous Isopeptide Bond Formation as a Powerful Tool for Engineering Site-Specific Antibody-Drug Conjugates."
Stranges et al., 2016, Proc Natl Acad Sci U S A 113, E6749-E6756, "Design and characterization of a nanopore-coupled polymerase for single-molecule DNA sequencing by synthesis on an electrode array."
Sun F et al, Proc Natl Acad Sci U S A. Aug. 5, 2014;111(31):11269-74, "Synthesis of bioactive protein hydrogels by genetically encoded SpyTag-SpyCatcher chemistry."
Thrane et al., 2016, Journal of nanobiotechnology 14, 30, "Bacterial superglue enables easy development of efficient virus-like particle based vaccines."
Veggiani et al., 2016 Proc Natl Acad Sci U S A 113, 1202-1207, "Programmable polyproteams built using twin peptide superglues."
Walden M et al, Elife. Jun. 2, 2015;4, "An internal thioester in a pathogen surface protein mediates covalent host binding."
Wang J et al, Biotechnol Biofuels. Mar. 31, 2016;9:79, "Enhanced thermal stability of lichenase from Bacillus subtilis 168 by SpyTag/SpyCatcher-mediated spontaneous cyclization."
Wang XW, Zhang WB., Angew Chem Int Ed Engl. Mar. 1, 2016;55(10):3442-6, "Cellular Synthesis of Protein Catenanes."
Xiong et al, Chinese Journal of Biochemistry and Molecular Biology (2016), 32 (10): 1141-1149, "The Effect of Solvent Properties to the Three-armed Star Elastin-like Polypeptides Phase Transition Temperature."
Zakeri B et al, J Am Chem Soc Apr. 7, 2010;132(13):4526-7, "Spontaneous Intermolecular Amide Bond Formation between Side Chains for Irreversible Peptide Targeting."
Zhang WB et al, J Am Chem Soc. Sep. 18, 2013;135(37):13988-97, "Controlling Macromolecular Topology with Genetically Encoded SpyTag-SpyCatcher Chemistry."

\* cited by examiner

A

B

A

B

POLYPEPTIDE AND ITS USE IN AFFINITY PURIFICATION

CROSS-REFERENCE TO RELATED APPLICATIONS

This application is the National Stage of International Application No. PCT/EP2019/083905, filed Dec. 5, 2019, which claims priority to GB 1819850.7, filed Dec. 5, 2018, which are entirely incorporated herein by reference.

The present invention relates to an affinity purification system comprising a polypeptide (protein) that binds selectively (e.g. specifically) and reversibly to its cognate peptide tag (ligand). In particular, the affinity purification system of the invention may be viewed as a two-part system comprising a polypeptide and its cognate peptide tag (affinity tag) that are capable of forming a stable and reversible non-covalent complex (i.e. a polypeptide:ligand complex) that can be dissociated under appropriate conditions to facilitate the purification of a molecule or component (fusion partner) conjugated or fused to said peptide tag. Nucleic acid molecules encoding said polypeptide, vectors comprising said nucleic acid molecules, and host cells comprising said vectors and nucleic acid molecules are also provided. An apparatus comprising said polypeptide immobilised on a solid substrate and a kit for preparing a solid substrate on which the polypeptide is immobilised are also provided. A process for purifying or isolating a molecule or component using the affinity purification system is also provided.

Affinity chromatography is a central enabling technology for research and for production of therapeutics, vaccines and diagnostics. However, a persistent problem with affinity tags is paradoxically the tags themselves, since the tags often perform no purpose post-purification. Tags, particularly peptide tags, can inhibit crystallization, interfere with protein interactions, and produce an unhelpful immune response in vivo. Tags may be removed by proteolysis but this extra step is time-consuming, often inefficient and reduces overall yield of the desired product.

There are already a multitude of affinity tags. However, each tag presents its own limitations. The most widely-used, the His-tag, is small and allows cost-effective purification. However, there are many examples of His-tagging disrupting protein solubility, structure and function, with particular challenges for proteins that require metal ions for their function in downstream biochemical assays and with the substantial immunogenicity of the His-tag. The four-amino acid C-tag is less immunogenic but is only functional at the C-terminus. Apart from purification, it would be desirable to use peptide tags for assembly or immobilization, but the low stability of peptide interactions is frequently limiting.

Proteins that are capable of spontaneous isopeptide bond formation have been used to develop peptide tag/binding partner pairs which covalently bind to each other and provide irreversible interactions (see e.g. WO2011/098772, WO 2016/193746 and WO2018/197854, herein incorporated by reference). In this respect, proteins which are capable of spontaneous isopeptide bond formation may be expressed as separate fragments, to give a peptide tag and a polypeptide binding partner for the peptide tag, where the two fragments are capable of covalently reconstituting by isopeptide bond formation, thereby linking molecules or components fused to the peptide tag and its polypeptide binding partner. The isopeptide bond formed by the peptide tag and its polypeptide binding partner is stable under conditions where non-covalent interactions would rapidly dissociate, e.g. over long periods of time (e.g. weeks), at high temperature (to at least 95° C.), at high force, or with harsh chemical treatment (e.g. pH 2-11, organic solvent, detergents or denaturants).

In brief, a peptide tag and its polypeptide binding partner (a so-called peptide tag/binding partner pair) may be derived from a protein capable of spontaneously forming an isopeptide bond (an isopeptide protein), wherein the domains of the protein are expressed separately to produce a peptide tag that comprises one of the residues involved in the isopeptide bond (e.g. an aspartate) and a polypeptide binding partner (or "catcher") that comprises the other residue involved in the isopeptide bond (e.g. a lysine) and at least one other residue required to form the isopeptide bond (e.g. a glutamate). Mixing the peptide tag and binding partner results in the spontaneous formation of an isopeptide bond between the tag and binding partner. Thus, by separately fusing the peptide tag and binding partner to different molecules or components, e.g. proteins, it is possible to covalently link said molecules or components together via an isopeptide bond formed between the peptide tag and binding partner, i.e. to form a linker between the molecules or components fused to the peptide tag and binding partner.

A peptide tag/binding partner pair, termed SpyTag/SpyCatcher, has been derived from the CnaB2 domain of the *Streptococcus pyogenes* FbaB protein (Zakeri et al., 2012, Proc Natl Acad Sci USA 109, E690-697) and used in diverse applications, including biomaterials (Botyanszki et al., 2015, Biotechnology and bioengineering 112, 2016-2024; Chen et al., 2014, Proc Natl Acad Sci USA 108, 11399-11404), next generation sequencing (Stranges et al., 2016, Proc Natl Acad Sci USA 113, E6749-E6756), enzyme stabilization (Schoene et al., 2016, Scientific reports 6, 21151) and vaccine development (Brune et al., 2016, Scientific reports 6, 19234; Thrane et al., 2016, Journal of nanobiotechnology 14, 30). A peptide tag/binding partner pair with improved reaction rate, termed SpyTag002/SpyCatcher002, has also been described (WO2018/197854).

However, these SpyTag/SpyCatcher systems still require the use of a separate purification tag (e.g. His-tag or C-tag) to enable isolation of each component for reaction or for isolation of the subsequent reaction product, i.e. the SpyTag/SpyCatcher isopeptide bond conjugate. Using additional purification tags in this manner increases the cloning effort and adds immunogenic sequences which may need to be removed before use in some applications, e.g. for vaccine generation. Thus, there is a desire to develop a system which can provide high affinity reversible binding of isopeptide bond-forming peptide tags, such as SpyTag, to allow for efficient purification, whilst also providing utility after purification, thus avoiding the need for removal of the tag or the simultaneous use of additional protein modifications.

The present inventors have now developed an affinity purification system (e.g. an affinity chromatography process) that allows SpyTag (and variants thereof) to have a dual functionality, i.e. to serve as a purification tag in addition to the current conjugation tag function. This avoids the need to modify SpyTag fusion proteins with additional affinity tags, which may need to be removed from the SpyTag/SpyCatcher reaction product post-purification, e.g. to avoid immunogenicity against the affinity tag. It has surprisingly been determined that a system which provides highly specific reversible non-covalent binding can be produced by introducing mutations into the SpyCatcher polypeptide sequences (SpyCatcher and SpyCatcher002). This results in a mutant "unreactive" SpyCatcher polypeptide (termed SpyDock) that allows SpyTag (and variants thereof) to be used for protein purification, via the reversible binding between the mutant SpyCatcher (SpyDock) and SpyTag-fusions. These SpyTag-fusions can then be isolated from the mutant SpyCatcher (SpyDock) with high purity for future use, e.g. to react covalently with SpyCatcher polypeptides.

In order to establish a SpyTag affinity purification system (termed Spy&Go), the inventors determined that selected mutations in the SpyCatcher polypeptides at the position of the activating glutamic acid residue in the CnaB2 triad were sufficient to abrogate the formation of an isopeptide bond between SpyCatcher and SpyTag, whilst maintaining a selective, stable and reversible non-covalent interaction. The inventors further established that additional mutations to the SpyCatcher polypeptide improved the utility of the interaction between the "unreactive" SpyCatcher polypeptide and SpyTag. The additional mutations ensure that the interaction can be formed efficiently even with low concentrations of tag-fusions in cell lysate and disrupted selectively to make possible the effective purification of SpyTag-fusions. As shown in detail in the Examples, the inventors surprisingly determined that the modified "unreactive" SpyCatcher polypeptide (SpyDock) enabled purification of SpyTag-MBP (maltose binding protein) with higher purity (98.9%) than via His-Tag:Ni-NTA purification (66.4%). Advantageously, the inventors also determined that the introduction of a unique cysteine residue in the modified "unreactive" Spy-Catcher enabled efficient coupling of the modified polypeptide (SpyDock, SEQ ID NO: 6) to a solid substrate with minimal disruption to SpyTag binding. The inventors have further shown that polypeptide of the invention immobilised on a solid substrate is stable in long-term storage under suitable conditions, e.g. aseptic (e.g. anti-bacterial) conditions such as in 20% ethanol at 10° C. or less (e.g. about 4° C.). Moreover, the inventors have determined that a solid substrate on which the polypeptide of the invention is immobilised may be regenerated and re-used multiple times without significant loss of purification activity.

Thus, in one aspect, the present invention provides a polypeptide comprising:

(i) an amino acid sequence as set forth in SEQ ID NO: 1, wherein X at position 79 is selected from alanine, glycine, serine, asparagine or threonine;

(ii) a portion of (i) comprising an amino acid sequence as set forth in SEQ ID NO: 2, wherein X at position 56 is selected from alanine, glycine, serine, asparagine or threonine;

(iii) an amino acid sequence with at least 80% sequence identity to a sequence as set forth in SEQ ID NO: 1, wherein the polypeptide comprises alanine, glycine, serine, asparagine or threonine at a position equivalent to position 79 of SEQ ID NO: 1; or (iv) a portion of (iii) comprising an amino acid sequence with at least 80% sequence identity to a sequence as set forth in SEQ ID NO: 2, wherein the polypeptide comprises alanine, glycine, serine, asparagine or threonine at a position equivalent to position 56 of SEQ ID NO: 2, wherein the polypeptide binds selectively and reversibly to a peptide comprising an amino acid sequence as set forth in SEQ ID NO: 3, 4 or 5.

In some embodiments, X at a position equivalent to position 79 of SEQ ID NO: 1 or position 56 of SEQ ID NO: 2 is selected from alanine, glycine or serine and preferably is alanine.

In a preferred embodiment, the polypeptide comprises alanine at a position equivalent to position 79 of SEQ ID NO: 1, such that the polypeptide comprises an amino acid sequence as set forth in SEQ ID NO: 6.

As mentioned above, the inventors have determined that the mutation of particular residues of the SpyCatcher polypeptides improved their utility in affinity purification via the non-covalent interaction between the polypeptide of the invention and SpyTag (e.g. SEQ ID NOs: 3, 4 or 5). Thus, in some embodiments, the polypeptide of the invention defined above may comprise a glutamic acid at a position equivalent to position 110 of SEQ ID NO: 1 or at a position equivalent to position 87 of SEQ ID NO: 2.

In some embodiments, the polypeptide of the invention defined above may comprise a proline at a position equivalent to position 91 of SEQ ID NO: 1 or at a position equivalent to position 68 of SEQ ID NO: 2.

In some embodiments, the polypeptide of the invention defined above may comprise an aspartic acid at a position equivalent to position 99 of SEQ ID NO: 1 or at a position equivalent to position 76 of SEQ ID NO: 2.

In some embodiments, the polypeptide of the invention defined above may comprise a lysine at a position equivalent to position 33 of SEQ ID NO: 1 or at a position equivalent to position 10 of SEQ ID NO: 2.

Thus, in a particular embodiment, the polypeptide comprises:

(i) an amino acid sequence as set forth in SEQ ID NO: 1, wherein X at position 79 is selected from alanine, glycine, serine, asparagine, or threonine;

(ii) a portion of (i) comprising an amino acid sequence as set forth in SEQ ID NO: 2, wherein X at position 56 is selected from alanine, glycine, serine, asparagine or threonine;

(iii) an amino acid sequence with at least 80% sequence identity to a sequence as set forth in SEQ ID NO: 1, wherein the polypeptide comprises alanine, glycine, serine, asparagine or threonine at a position equivalent to position 79 of SEQ ID NO: 1 and one or more (preferably all) of the following:

(1) lysine at a position equivalent to position 33 of SEQ ID NO: 1;

(2) proline at a position equivalent to position 91 of SEQ ID NO: 1;

(3) aspartic acid at a position equivalent to position 99 of SEQ ID NO: 1; and (4) glutamic acid ata position equivalent to position 110 of SEQ ID NO: 1; or (iv) a portion of (iii) comprising an amino acid sequence with at least 80% sequence identity to a sequence as set forth in SEQ ID NO: 2, wherein the polypeptide comprises alanine, glycine, serine, asparagine or threonine at a position equivalent to position 56 of SEQ ID NO: 2 and one or more (preferably all) of the following:

(1) lysine at a position equivalent to position 10 of SEQ ID NO: 2;

(2) proline at a position equivalent to position 68 of SEQ ID NO: 2;

(3) aspartic acid at a position equivalent to position 76 of SEQ ID NO: 2; and (4) glutamic acid at a position equivalent to position 87 of SEQ ID NO: 2, wherein the polypeptide binds selectively and reversibly to a peptide comprising an amino acid sequence as set forth in SEQ ID NO: 3, 4 or 5.

The polypeptide of the invention is based on a variant on the SpyCatcher polypeptide (SEQ ID NO: 10). The variant, known as SpyCatcher002 (SEQ ID NO: 11), contains various mutations relative to SpyCatcher and it may be advantageous to retain the mutations in the polypeptide of the invention. Accordingly, in some embodiments the polypeptide comprises an amino acid sequence with at least 80% sequence identity to a sequence as set forth in SEQ ID NO: 1, wherein the amino acid sequence comprises lysine at position 33, proline at position 91, aspartic acid at position 99, glutamic acid at position 110 and one or more of the following:
- i) threonine at position 4;
- ii) glycine at position 11;
- iii) proline at position 15;
- iv) threonine at position 21;
- v) arginine at position 39;
- iiv) histidine at position 64;
- vii) glutamic acid at position 107; and
- viii) threonine at position 115, wherein the specified amino acid residues are at positions equivalent to the positions in SEQ ID NO: 1.

In some embodiments, the polypeptide comprises an amino acid sequence with at least 80% sequence identity to a sequence as set forth in SEQ ID NO: 2 and wherein the amino acid sequence comprises lysine at position 10, proline at position 68, aspartic acid at position 76, glutamic acid at position 87 and one or more of the following:
- i) arginine at position 16;
- ii) histidine at position 41;
- iii) glutamic acid at position 84; and
- iv) threonine at position 92, wherein the specified amino acid residues are at positions equivalent to the positions in SEQ ID NO: 2.

Thus, in some embodiments the polypeptide comprises an amino acid sequence with at least 80% sequence identity to a sequence as set forth in SEQ ID NO: 1, wherein the amino acid sequence comprises lysine at position 33, proline at position 91, aspartic acid at position 99, glutamic acid at position 110 and any two, three, four, five, six, seven or eight of the following:
- i) threonine at position 4;
- ii) glycine at position 11;
- iii) proline at position 15;
- iv) threonine at position 21;
- v) arginine at position 39;
- vi) histidine at position 64;
- vii) glutamic acid at position 107; and
- viii) threonine at position 115, wherein the specified amino acid residues are at positions equivalent to the positions in SEQ ID NO: 1.

In some embodiments, the polypeptide comprises an amino acid sequence with at least 80% sequence identity to a sequence as set forth in SEQ ID NO: 2 and wherein the amino acid sequence comprises lysine at position 10, proline at position 68, aspartic acid at position 76, glutamic acid at position 87 and any two, three or four of the following:
- i) arginine at position 16;
- ii) histidine at position 41;
- iii) glutamic acid at position 84; and
- iv) threonine at position 92, wherein the specified amino acid residues are at positions equivalent to the positions in SEQ ID NO: 2.

It is contemplated that the polypeptide of the invention may comprise any one or any combination of the specified amino acid residues defined above (e.g. any combination of two, three, four, five, six, seven, eight, nine, ten, eleven or twelve of the amino acid residues specified above), e.g. 1) and 2), 1) and 3), 1 and 4), 2) and 3), 3) and 4), 1), 2) and 3), 1), 3) and 4), 1), 2) and 4), 2), 3) and 4) etc. in combination with any of i)-viii), e.g. i) and ii), i) and iii), i) and iv), i) and v), i) and vi), ii) and iii), ii) and iv) etc., i), ii) and iii), i), iii) and iv), i), iii) and v) etc. However, in particularly preferred embodiments the polypeptide comprises:

(A) an amino acid sequence with at least 80% sequence identity to a sequence as set forth in SEQ ID NO: 1, wherein the amino acid sequence comprises lysine at position 33, proline at position 91, aspartic acid at position 99, glutamic acid at position 110 and all of the following:
- i) threonine at position 4;
- ii) glycine at position 11;
- iii) proline at position 15;
- iv) threonine at position 21;
- v) arginine at position 39;
- vi) histidine at position 64;
- vii) glutamic acid at position 107; and
- viii) threonine at position 115, wherein the specified amino acid residues are at positions equivalent to the positions in SEQ ID NO: 1; or (B) an amino acid sequence with at least 80% sequence identity to a sequence as set forth in SEQ ID NO: 2 and wherein the amino acid sequence comprises lysine at position 10, proline at position 68, aspartic acid at position 76, glutamic acid at position 87 and all of the following:
- i) arginine at position 16;
- ii) histidine at position 41;
- iii) glutamic acid at position 84; and
- iv) threonine at position 92, wherein the specified amino acid residues are at positions equivalent to the positions in SEQ ID NO: 2.

As discussed above, the inventors have further determined that the presence of a cysteine residue in the polypeptide of the invention advantageously enables efficient coupling of the polypeptide to a solid substrate with minimal disruption to SpyTag (SEQ ID NO: 3, 4 or 5) non-covalent binding. Thus, in some embodiments, the polypeptide variants defined above may also comprise a cysteine at a position equivalent to position 51 in SEQ ID NO: 1 or position 28 in SEQ ID NO: 2.

The polypeptide of the invention binds selectively and reversibly to its cognate peptide tag (i.e. SpyTag peptide or a variant thereof), such as a peptide comprising an amino acid sequence as set forth in SEQ ID NOs: 3, 4 or 5, under suitable conditions.

The term "binds selectively" refers to the ability of the polypeptide to bind non-covalently (e.g. by van der Waals forces and/or hydrogen-bonding) to its cognate peptide tag with greater affinity and/or specificity than to other components in the sample in which the peptide tag is present (e.g. the sample from which the peptide tag (and associated molecule or component to which the peptide tag is fused or conjugated, i.e. fusion partner) is to be isolated or purified). Thus, the polypeptide of the invention may alternatively be viewed as binding specifically and reversibly to its cognate peptide tag (i.e. SpyTag peptide or a variant thereof), such as a peptide comprising an amino acid sequence as set forth in SEQ ID NOs: 3, 4 or 5, under suitable conditions.

Binding to the cognate peptide tag may be distinguished from binding to other molecules (e.g. peptides or polypeptides) present in the sample, i.e. non-cognate molecules. The polypeptide of the invention either does not bind to other molecules (e.g. peptides or polypeptides) present in the sample or does so negligibly or non-detectably that any such non-specific binding, if it occurs, readily may be distinguished from binding to the cognate peptide tag.

In particular, if the polypeptide of the invention binds to molecules other than the cognate peptide tag, such binding must be transient and the binding affinity must be less than the binding affinity of the polypeptide for the cognate peptide tag. Thus, the binding affinity of polypeptide for the peptide tag should be at least an order of magnitude more than the other molecules (i.e. non-cognate molecules) present in the sample. Preferably, the binding affinity of the polypeptide for the cognate peptide tag should be at least 2, 3, 4, 5, or 6 orders of magnitude more than the binding affinity for non-cognate molecules (e.g. peptides or polypeptides).

Thus, selective or specific binding refers to affinity of the polypeptide of the invention for its cognate peptide tag where the dissociation constant of the polypeptide for the cognate peptide tag is less than about $10^{-3}$M. In a preferred embodiment the dissociation constant of the polypeptide for its cognate peptide tag is less than about $10^{-4}$M, $10^{-5}$M, $10^{-6}$M, $10^{-7}$M, $10^{-8}$M or $10^{-9}$M.

The binding selectivity (e.g. specificity) of the polypeptide of the invention may also be defined based on the yield and/or purity of the product, i.e. the cognate peptide tag and associated molecule or component (fusion partner, e.g. polypeptide), to which the peptide tag is fused or conjugated, obtained in the isolation or purification process defined below. In some embodiments, the polypeptide of the invention in the process defined below results in a product with a purity of at least about 75%, such as at least about 80%, 85%, 90%, 95%, 96%, 97% or 98%. The purity of the product obtained using the process and polypeptide of the invention may be determined using any suitable means, such as the SDS-PAGE method described in the Examples below.

In some embodiments, the polypeptide of the invention in the process defined below results in a product with a yield of at least about 50%, such as about 60%, 70%, 75%, 80% 85% or 90%. The yield of the product obtained using the process and polypeptide of the invention may be determined using any suitable means.

The term "cognate" refers to components that function or specifically interact together. Thus, in the context of the present invention, a cognate pair refers to a peptide tag (i.e. SpyTag or a variant thereof, such as a peptide comprising or consisting of SEQ ID NOs: 3, 4 and 5) and the polypeptide of the invention that bind non-covalently to form a complex (i.e. a polypeptide:peptide tag complex).

Thus, a cognate peptide tag refers to a SpyTag peptide or variant thereof (e.g. a peptide comprising an amino acid sequence set forth in one of SEQ ID NOs: 3-5) to which the polypeptide of the invention can bind selectively (e.g. specifically) and reversibly. In some embodiments, the cognate peptide tag may be a peptide comprising an amino acid sequence with at least 80% sequence identity to an amino acid sequence as set forth in one of SEQ ID NOs: 3-5. In a preferred embodiment, the cognate peptide tag is capable of spontaneously forming an isopeptide bond with a polypeptide comprising an amino acid sequence as set forth in SEQ ID NO: 10 or 11, e.g. between an aspartic acid in the cognate peptide tag (i.e. an aspartic acid at position equivalent to position 8 in SEQ ID NO: 3, position 7 in SEQ ID NO: 4 or position 10 in SEQ ID NO: 5) and the lysine residue at position 33 of SEQ ID NO: 10 or SEQ ID NO: 11. In some embodiments, the cognate peptide tag may not be capable of spontaneously forming an isopeptide bond with a polypeptide comprising an amino acid sequence as set forth in SEQ ID NO: 10 or 11, e.g. because it does not contain an aspartic acid residue capable of reacting with the lysine residue at position 33 of SEQ ID NO: 10 or SEQ ID NO: 11. Such cognate peptide tags may find utility as negative control peptides in the isolation or purification process of the invention, described below.

Thus, a polypeptide of the invention must bind selectively and reversibly to at least one peptide comprising or consisting of an amino acid as set forth in SEQ ID NOs: 3-5. In a preferred embodiment, polypeptide of the invention must bind selectively and reversibly to each peptide comprising or consisting of an amino acid as set forth in SEQ ID NOs: 3-5. Thus, the polypeptide of the invention binds to at least one (preferably all) peptide(s) comprising or consisting of an amino acid sequence as set forth in SEQ ID NOs: 3-5 with greater affinity and/or specificity than to other components in the sample (i.e. non-cognate molecules) in which the peptide tag is present. A sample may be any sample (e.g. cell lysate etc. as described below) from which the peptide tag (and associated molecule or component to which the peptide tag is fused or conjugated, i.e. fusion partner) is to be isolated or purified. However, the polypeptide of the invention may also bind to other cognate peptide tags as defined herein.

Alternatively viewed, the polypeptide variants of the invention (variants of SEQ ID NO: 1 as defined herein) must be capable of competing with a polypeptide comprising an amino acid sequence set forth in SEQ ID NO: 6 (SpyDock) for binding with a cognate peptide tag as defined herein, e.g. one or all of SEQ ID NOs: 3-5. Any suitable competition assay known in the art may be used to determine whether polypeptide variants of the invention compete with SpyDock.

A non-cognate molecule, particularly a non-cognate peptide or polypeptide may be defined as a peptide or polypeptide that does not contain an amino acid sequence consisting of an amino acid sequence with at least 60% sequence identity to a SpyTag peptide, such as SEQ ID NOs: 3, 4 or 5. Preferably, the non-cognate molecule does not contain consecutive sequence of 12-16 amino acids with more than about 60%, 55%, 50%, 45%, 40%, 35%, 30%, 25% or 20% sequence identity to a SpyTag peptide, such as SEQ ID NOs: 3, 4 or 5. Other non-cognate molecules include carbohydrates, sugars, lipids, ions and small molecules.

Suitable conditions for the selective or specific binding of the polypeptide to its cognate peptide tag are set out below. However, it is evident from the Examples below that the polypeptide of the invention is able to selectively and specifically bind its cognate peptide tag under a range of conditions.

For instance, the polypeptide may bind selectively (e.g. specifically) to its cognate peptide tag in a variety of buffers including phosphate buffered saline (PBS), 4-(2-hydroxyethyl)-1-piperazineethanesulfonic acid (HEPES), HEPES buffered saline (HBS), Tris-phosphate and Tris buffered saline (TBS), both with and without EDTA. Detergents such as Tween 20 and Triton X-100 may also be present, as may denaturants such as urea (e.g. less than 4M urea) and guanidine hydrochloride (e.g. less than 2M guanidine hydrochloride). Binding may occur at a pH of about 3.0-8.0, e.g. 4.0-7.0, 5.0-7.0, such as about 5.5-6.5, over a wide range of temperatures, e.g. 0-40° C., e.g. 1, 2, 3, 4, 5, 10, 12, 15, 18, 20, 22, 25, 28, 30, 35 or 37° C., preferably about 4-10° C., e.g. about 4° C. The skilled person would readily be able to determine other suitable conditions.

Thus, in some embodiments, conditions that are suitable for selective (e.g. specific) binding between the polypeptide of the invention and its cognate peptide tag include any conditions in which contacting the polypeptide of the invention with its cognate peptide tag (e.g. a sample comprising the cognate peptide tag) results in the formation of non-covalent complex between polypeptide and cognate peptide tag. For instance, contacting said polypeptide and cognate peptide tag in buffered conditions, e.g. in a buffered solution or on a solid phase (e.g. column) that has been equilibrated with a buffer, such as TBS. The step of contacting may be at any suitable pH, such as pH 3.0-8.0, e.g. 4.0-7.0, such as pH 4.2, 4.4, 4.6, 4.8, 5.0, 5.2, 5.4, 5.6, 5.8, 6.0, 6.2, 6.4, 6.6, 6.8 or 7.0. Additionally or alternatively, the step of contacting may be at any suitable temperature, such as about 0-40° C., e.g. about 1-39, 2-38, 3-37, 4-36, 5-35, 6-34, 7-33, 8-32, 9-31 or 10-30° C., e.g. about 10, 12, 15, 18, 20, 22, 25, 28, 30, 33, 35 or 37° C., preferably about 4-10° C., e.g. about 4° C.

The term "reversible" or "binds reversibly" refers to ability of the interaction between the polypeptide and its cognate peptide tag to be disrupted, resulting in the separation (dissociation) of the complex under suitable conditions. In other words, the non-covalent interaction formed by the polypeptide:cognate peptide tag complex can be broken under suitable conditions to enable the separation of the constituent parts. Suitable conditions to dissociate the complex may include any conditions that are able to disrupt or break the non-covalent bonds required to form the complex. An example of suitable conditions that may be used in the process of the invention is set out below.

It will be evident that conditions to dissociate the polypeptide:cognate peptide tag complex preferably should not lead to irreversible loss of activity of the SpyTag peptide and/or fusion partner. For instance, conditions that prevent SpyTag from reacting spontaneously with a SpyCatcher polypeptide to form an isopeptide bond should be avoided. Similarly, conditions that alter or inhibit (e.g. denature) the molecule or component fused to the SpyTag peptide (i.e. fusion partner, e.g. polypeptide) are not suitable for dissociating polypeptide:cognate peptide tag complex, as such conditions would limit the utility of SpyTag fusion in downstream applications. Such conditions will depend on the nature of the fusion partner and the skilled person readily could determine which conditions are suitable (or unsuitable) based on methods known in the art. By way of example, boiling the polypeptide:cognate peptide tag complex and/or treatment with 1% SDS would dissociate the polypeptide:cognate peptide tag complex, but may irreversibly alter (e.g. denature) the fusion partner.

The term "spontaneous" as used herein refers to an isopeptide bond, which can form in a protein or between a peptide and protein, e.g. the cognate peptide tag described herein and a polypeptide comprising an amino acid sequence as set forth in SEQ ID NO: 10 or 11 without any other agent (e.g. an enzyme catalyst) being present and/or without chemical modification of the protein or peptide, e.g. without native chemical ligation or chemical coupling using 1-ethyl-3-(3-dimethylaminopropyl) carbodiimide (EDC). Thus, native chemical ligation to modify a peptide or protein having a C-terminal thioester is not carried out.

Thus, a spontaneous isopeptide bond can form between a cognate peptide tag as described herein and a polypeptide (e.g. a polypeptide comprising an amino acid sequence as set forth in SEQ ID NO: 10 or 11) when in isolation and without chemical modification of the cognate peptide tag and/or the polypeptide with which it reacts. A spontaneous isopeptide bond may therefore form of its own accord in the absence of enzymes or other exogenous substances and without chemical modification of the cognate peptide tag described herein and the polypeptide with which it reacts.

A spontaneous isopeptide bond may form almost immediately after contact of the reactive peptide tag and polypeptide, e.g. within 1, 2, 3, 4, 5, 10, 15, 20, 25 or 30 minutes, or within 1, 2, 4, 8, 12, 16, 20 or 24 hours.

The polypeptide of the invention encompasses mutant forms (i.e. referred to herein as homologues, variants or derivatives), which are structurally similar to the exemplified polypeptides set forth in SEQ ID NOs: 6 and 7, respectively. The polypeptide variants of the invention are able to bind selectively and reversibly to the cognate peptide tag under suitable conditions as defined above.

In cases where a polypeptide variant comprises mutations, e.g. deletions or insertions, relative to SEQ ID NOs: 6 and 7, the residues specified above are present at equivalent amino acid positions in the variant polypeptide sequences. In some embodiments, deletions in the polypeptide variants of the invention are not N-terminal and/or C-terminal truncations.

However, as mentioned above, it is contemplated that the polypeptide exemplified herein (i.e. SEQ ID NO: 6) and variants thereof may be truncated at the N-terminus and/or C-terminus without significantly reducing the activity of the polypeptide. In particular, SEQ ID NO: 6 may be truncated by up to 23 amino acids at the N-terminus to provide a polypeptide as set forth in SEQ ID NO: 7. Additionally or alternatively, in some embodiments the polypeptide set forth in SEQ ID NO: 6 may be truncated by less than 23 amino acids, e.g. 5, 10, 15 or 20 amino acids. In some embodiments, the polypeptide and portion exemplified herein (i.e. SEQ ID NOs: 6 and 7, respectively) may be truncated by up to 9 amino acids at the C-terminus (e.g. 1, 2, 3, 4, 5, 6, 7, 8 or 9 amino acids), preferably by 8 amino acids or fewer. Thus, the term variant as used herein includes truncation variants of the exemplified polypeptides. In a particularly preferred embodiment, the truncated variant polypeptide of the invention comprises an amino acid sequence as set forth in SEQ ID NO: 7 or a variant thereof, as discussed above.

As referred to herein a "portion" comprises at least an amino acid sequence as set forth in SEQ ID NO: 7 optionally further truncated at the C-terminal end, i.e. at least 83, 84, 85, 86, 87, 88, 89, 90, 95, 100, 105, 110 or more amino acids of SEQ ID NO: 6 (the sequence from which it is derived), preferably containing an amino acid sequence as set forth in SEQ ID NO: 7. Thus, said portion may be obtained from a central or N-terminal or C-terminal portion of the sequence. Preferably said portion is obtained from the central portion, i.e. it comprises an N-terminal and/or C-terminal truncation as defined above. Notably, "portions" as described herein are polypeptides of the invention and therefore satisfy the identity (relative to a comparable region) conditions and functional equivalence conditions mentioned herein.

An equivalent position in the polypeptide of the invention is preferably determined by reference to the amino acid sequence of SEQ ID NO: 1. The homologous or corresponding position can be readily deduced by lining up the sequence of the homologue (mutant, variant or derivative) polypeptide and the sequence of SEQ ID NO: 1 based on the homology or identity between the sequences, for example using a BLAST algorithm.

In some embodiments, a polypeptide variant of the present invention may differ from SEQ ID NO: 1 by, for example, 1 to 50, 1 to 45, 1 to 40, 1 to 35, 1 to 30, 1 to 25, 1 to 20, 1 to 15, 1 to 10, 1 to 8, 1 to 6, 1 to 5, 1 to 4, e.g. 1, 2 or 3 amino acid substitutions, insertions and/or deletions, preferably 1 to 23, 1 to 20, 1 to 15, 1 to 10, 1 to 8, 1 to 6, 1 to 5, 1 to 4, e.g. 1, 2 to 3 amino acid substitutions and/or 1 to 33, 1 to 30, 1 to 25, 1 to 20, 1 to 15, 1 to 10, 1 to 8, 1 to 6, 1 to 5, 1 to 4, e.g. 1, 2 or 3 amino acid deletions. As discussed below, in some embodiments, it is preferred that deletions are at the N- and/or C-terminus, i.e. truncations, thereby generating polypeptide portions of SEQ ID NO: 1 as defined above, such as the portions disclosed in SEQ ID NOs: 2 and 7.

In some embodiments, any mutations that are present in the polypeptide of the present invention relative to the exemplified polypeptide (SEQ ID NO: 6) may be conservative amino acid substitutions. A conservative amino acid substitution refers to the replacement of an amino acid by another which preserves the physicochemical character of the polypeptide (e.g. D may be replaced by E or vice versa, N by Q, or L or I by V or vice versa). Thus, generally the substituting amino acid has similar properties, e.g. hydrophobicity, hydrophilicity, electronegativity, bulky side chains etc. to the amino acid being replaced. Isomers of the native L-amino acid e.g. D-amino acids may be incorporated.

In some embodiments, a cognate peptide tag variant as defined herein may differ from SEQ ID NOs: 3-5 by, for example, 1 to 5, 1 to 4, e.g. 1, 2 to 3 amino acid substitutions, insertions and/or deletions, preferably substitutions, as defined above.

In some embodiments, said cognate peptide tag sequence described herein is at least 85, 90, 95, 96, 97, 98, 99 or 100% identical to the sequence (SEQ ID NOs: 3-5) to which it is compared.

In some embodiments, said polypeptide sequence above is at least 85, 90, 95, 96, 97, 98, 99 or 100% identical to the sequence (SEQ ID NOs: 1 or 2) to which it is compared.

Sequence identity may be determined by any suitable means known in the art, e.g. using the SWISS-PROT protein sequence databank using FASTA pep-cmp with a variable pamfactor, and gap creation penalty set at 12.0 and gap extension penalty set at 4.0, and a window of 2 amino acids. Other programs for determining amino acid sequence identity include the BestFit program of the Genetics Computer Group (GCG) Version 10 Software package from the University of Wisconsin. The program uses the local homology algorithm of Smith and Waterman with the default values: Gap creation penalty–8, Gap extension penalty=2, Average match=2.912, Average mismatch=–2.003.

Preferably said comparison is made over the full length of the sequence, but may be made over a smaller window of comparison, e.g. less than 100, 80 or 50 contiguous amino acids.

Preferably the cognate peptide tag and polypeptide variants (e.g. sequence identity-related variants) are functionally equivalent to the cognate peptide tag and polypeptide having a sequence as set forth in SEQ ID NOs: 3-5 or SEQ ID NOs: 6 or 7, respectively.

As referred to herein, "functional equivalence" refers to variants of the cognate peptide tag described herein and polypeptide of the invention discussed above that may show some reduced selectively (e.g. specificity) or affinity in the binding (formation of the non-covalent complex) with its respective partner (e.g. lower purity or yield in the process of the invention, or activity in a limited range of reaction conditions (e.g. narrower temperature range, such as 10-30° C. etc.)) relative to the parent molecule (i.e. the molecule with which it shows sequence homology), but preferably are as efficient or are more efficient.

A mutant or variant cognate peptide tag described herein with activity that is "equivalent" to the activity of a cognate peptide tag comprising or consisting of an amino acid sequence as set forth in one of SEQ ID NOs: 3-5 may have activity that is similar (i.e. comparable) to the activity of a peptide tag comprising or consisting of an amino acid sequence as set forth in one of SEQ ID NOs: 3-5, i.e. such that the practical applications of the peptide tag are not significantly affected, e.g. within a margin of experimental error.

Thus, an equivalent peptide tag activity means that the mutant or variant cognate peptide tag described is capable of binding selectively and reversibly to the polypeptide of the invention (particularly a polypeptide comprising an amino acid sequence as set forth in SEQ ID NO: 6 or 7). In some preferred embodiments, the mutant or variant cognate peptide tag is capable of spontaneously forming an isopeptide bond with a polypeptide comprising or consisting of an amino acid sequence as set forth in SEQ ID NO: 10 or 11 with a similar reaction rate (i.e. rate constant as discussed below) and/or yield to a peptide tag comprising or consisting of an amino acid sequence as set forth in one of SEQ ID NOs: 3-5 under the same conditions.

Similarly, a mutant or variant polypeptide of the invention with activity that is "equivalent" to the activity of a polypeptide comprising or consisting of an amino acid sequence as set forth in SEQ ID NO: 6 or 7 (preferably SEQ ID NO: 6) may have activity that is similar (i.e. comparable) to the activity of a polypeptide comprising or consisting of an amino acid sequence as set forth in SEQ ID NO: 6 or 7 (preferably SEQ ID NO: 6), i.e. such that the practical applications of the polypeptide are not significantly affected, e.g. within a margin of experimental error. Thus, an equivalent polypeptide activity means that the mutant or variant polypeptide of the invention is capable of binding selectively and reversibly to the cognate peptide tag described herein (e.g. comprising or consisting of an amino acid sequence as set forth in one of SEQ ID NOs: 3-5) with a similar affinity and/or yield, as described above, to a polypeptide comprising or consisting of an amino acid sequence as set forth in SEQ ID NO: 6 or 7 (preferably SEQ ID NO: 6) under the same conditions.

A mutant or variant polypeptide of the invention with activity that is "equivalent" to the activity of a polypeptide comprising or consisting of an amino acid sequence as set forth in SEQ ID NO: 6 or 7 may compete with a polypeptide comprising or consisting of an amino acid sequence set forth in SEQ ID NO: 6 (SpyDock) for binding with a cognate peptide tag as defined herein, e.g. one or all of SEQ ID NOs: 3-5.

The activity of different polypeptides (e.g. SEQ ID NO: 6 versus mutant) measured under the same reaction conditions, e.g. temperature, ligands (i.e. cognate peptide tag sequence) and their concentration, buffer, salt etc. as exemplified above, can be readily compared to determine whether the affinity and/or yield for each polypeptide is higher, lower or equivalent.

Hence, any modification or combination of modifications may be made to SEQ ID NO: 1 to produce a variant polypeptide of the invention, provided that the variant polypeptide comprises an amino acid selected from alanine, glycine, serine, asparagine or threonine at a position equivalent to position 79. In some embodiments, the variant polypeptide comprises one or more (preferably all) of the following:

(1) lysine at a position equivalent to position 33 of SEQ ID NO: 1;

(2) proline at a position equivalent to position 91 of SEQ ID NO: 1;

(3) aspartic acid at a position equivalent to position 99 of SEQ ID NO: 1; and (4) glutamic acid ata position equivalent to position 110 of SEQ ID NO: 1; and optionally at least one (preferably 2, 3, 4, 5, 6 or 7) other amino acid residue(s) at positions equivalent to positions 4, 15, 39, 51, 64, 107, 115 of SEQ ID NO: 1 as defined above and retains the functional characteristics defined above, i.e. it results in a polypeptide that binds selectively and reversibly to a cognate peptide tag comprising or consisting of an amino acid sequence as set forth in one of SEQ ID NOs: 3-5 and optionally results in a process with an equivalent or higher purity and/or yield, temperature and/or buffer range relative to a polypeptide having an amino acid sequence as set forth in SEQ ID NO: 6.

Alternatively viewed, any modification or combination of modifications (preferably substitutions) may be made to SEQ ID NO: 7 to produce a variant polypeptide of the invention, provided that the variant polypeptide comprises an amino acid selected from alanine, glycine, serine, asparagine, or threonine at a position equivalent to position 56. In some embodiments, the variant polypeptide comprises one or more (preferably all) of the following:

(1) lysine at a position equivalent to position 10 of SEQ ID NO: 7;

(2) proline at a position equivalent to position 68 of SEQ ID NO: 7;

(3) aspartic acid at a position equivalent to position 76 of SEQ ID NO: 7; and (4) glutamic acid at a position equivalent to position 111 of SEQ ID NO: 7; and optionally at least one (preferably 2, 3, 4 or 5) other amino acid residue(s) at positions equivalent to positions 16, 28, 41, 84, 92 of SEQ ID NO: 7 as defined above and retains the functional characteristics defined above, i.e. it results in a polypeptide that binds selectively and reversibly to a cognate peptide tag comprising or consisting of an amino acid sequence as set forth in one of SEQ ID NOs: 3-5 and optionally results in a process with an equivalent or higher purity and/or yield, temperature and/or buffer range relative to a polypeptide having an amino acid sequence as set forth in SEQ ID NO: 6 or 7.

The terms "tag" and "peptide tag" as used herein generally refer to a peptide.

The term "peptide tag binding partner", "binding partner" or "catcher" as used herein generally refers to a polypeptide or protein.

In this respect, there is no standard definition regarding the size boundaries between what is meant by peptide or polypeptide. Typically a peptide may be viewed as comprising between 2-39 amino acids. Accordingly, a polypeptide may be viewed as comprising at least 40 amino acids, preferably at least 50, 60, 70, 80, 90, 100 or 110 amino acids.

Thus, in preferred embodiments a peptide tag as defined herein may be viewed as comprising at least 12 amino acids, e.g. 12-39 amino acids, such as e.g. 13-35, 14-34, 15-33, 16-31, 17-30 amino acids in length, e.g. it may comprise or consist of 12, 13, 14, 15, 16, 17, 18, 19 or 20 amino acids.

A polypeptide of the invention as defined herein may be viewed as comprising at least 80 amino acids, e.g. 80-150 amino acids, such as e.g. 80-140, 80-130, 80-120 amino acids in length, e.g. it may comprise or consist of 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119 or 120 amino acids.

In a further embodiment, the invention provides a nucleic acid molecule comprising a nucleotide sequence which encodes a polypeptide of the invention as hereinbefore defined.

In some embodiments, the nucleic acid molecule encoding a polypeptide defined above comprises a nucleotide sequence as set forth in any one of SEQ ID NOs: 8 or 9 or a nucleotide sequence with at least 80% sequence identity to a sequence as set forth in any one of SEQ ID NOs: 8 or 9.

Preferably, the nucleic acid molecule above is at least 85, 90, 95, 96, 97, 98, 99 or 100% identical to the sequence to which it is compared.

Nucleic acid sequence identity may be determined by, e.g. FASTA Search using GCG packages, with default values and a variable pamfactor, and gap creation penalty set at 12.0 and gap extension penalty set at 4.0 with a window of 6 nucleotides. Preferably said comparison is made over the full length of the sequence, but may be made over a smaller window of comparison, e.g. less than 300, 200, 100 or 50 contiguous nucleotides.

The nucleic acid molecules of the invention may be made up of ribonucleotides and/or deoxyribonucleotides as well as synthetic residues, e.g. synthetic nucleotides, that are capable of participating in Watson-Crick type or analogous base pair interactions. Preferably, the nucleic acid molecule is DNA or RNA.

The nucleic acid molecules described above may be operatively linked to an expression control sequence, or a recombinant DNA cloning vehicle or vector containing such a recombinant DNA molecule. This allows cellular expression of the polypeptide of the invention as a gene product, the expression of which is directed by the gene(s) introduced into cells of interest. Gene expression is directed from a promoter active in the cells of interest and may be inserted in any form of linear or circular nucleic acid (e.g. DNA) vector for incorporation in the genome or for independent replication or transient transfection/expression. Suitable transformation or transfection techniques are well described in the literature. Alternatively, the naked nucleic acid (e.g. DNA or RNA, which may include one or more synthetic residues, e.g. base analogues) molecule may be introduced directly into the cell for the production of the polypeptide of the invention. Alternatively the nucleic acid may be converted to mRNA by in vitro transcription and the relevant protein may be generated by in vitro translation.

Appropriate expression vectors include appropriate control sequences such as for example translational (e.g. start and stop codons, ribosomal binding sites) and transcriptional control elements (e.g. promoter-operator regions, termination stop sequences) linked in matching reading frame with the nucleic acid molecules of the invention. Appropriate vectors may include plasmids and viruses (including both bacteriophage and eukaryotic viruses). Suitable viral vectors include baculovirus and also adenovirus, adeno-associated virus, herpes and vaccinia/pox viruses. Many other viral vectors are described in the art. Examples of suitable vectors include bacterial and mammalian expression vectors pGEX-KG, pEF-neo and pEF-HA.

In some embodiments the polypeptide of the invention may comprise additional sequences (e.g. peptide/polypeptide tags to facilitate purification of the polypeptide prior to use in the process and use of the invention discussed below). Any suitable purification moiety or tag may be incorporated into the polypeptide and such moieties are well known in the art. For instance, in some embodiments, the polypeptide may comprise a peptide purification tag or moiety, e.g. a His-tag sequence. Such purification moieties or tags may be incorporated at any position within the polypeptide. In some preferred embodiments, the purification moiety is located at or towards (i.e. within 5, 10, 15, 20 amino acids of) the N- or C-terminus of the polypeptide.) Accordingly, the nucleic acid molecule may conveniently be fused with DNA encoding an additional peptide or polypeptide, e.g. His-tag, maltose-binding protein, to produce a fusion protein on expression.

Thus viewed from a further aspect, the present invention provides a vector, preferably an expression vector, comprising a nucleic acid molecule as defined above.

Other aspects of the invention include methods for preparing recombinant nucleic acid molecules according to the invention, comprising inserting nucleic acid molecule of the invention encoding the polypeptide of the invention into vector nucleic acid.

Nucleic acid molecules of the invention, preferably contained in a vector, may be introduced into a cell by any appropriate means. Suitable transformation or transfection techniques are well described in the literature. Numerous techniques are known and may be used to introduce such vectors into prokaryotic or eukaryotic cells for expression. Preferred host cells for this purpose include insect cell lines, yeast, mammalian cell lines or *E. coli*, such as strain BL21/DE3. The invention also extends to transformed or transfected prokaryotic or eukaryotic host cells containing a nucleic acid molecule, particularly a vector as defined above.

Thus, in another aspect, there is provided a recombinant host cell containing a nucleic acid molecule and/or vector as described above.

By "recombinant" is meant that the nucleic acid molecule and/or vector has been introduced into the host cell. The host cell may or may not naturally contain an endogenous copy of the nucleic acid molecule, but it is recombinant in that an exogenous or further endogenous copy of the nucleic acid molecule and/or vector has been introduced.

A further aspect of the invention provides a method of preparing a polypeptide of the invention as hereinbefore defined, which comprises culturing a host cell containing a nucleic acid molecule as defined above, under conditions whereby said nucleic acid molecule encoding said polypeptide is expressed and recovering said polypeptide thus produced. The expressed polypeptide forms a further aspect of the invention.

In some embodiments, the polypeptide of the invention, or for use in the processes and uses of the invention, may be generated synthetically, e.g. by ligation of amino acids or smaller synthetically generated peptides, or more conveniently by recombinant expression of a nucleic acid molecule encoding said polypeptide as described hereinbefore.

Nucleic acid molecules of the invention may be generated synthetically by any suitable means known in the art.

Thus, the polypeptide of the invention may be an isolated, purified, recombinant or synthesised polypeptide.

The term "polypeptide" is used herein interchangeably with the term "protein". As noted above, the term polypeptide or protein typically includes any amino acid sequence comprising at least 40 consecutive amino acid residues, e.g. at least 50, 60, 70, 80, 90, 100, 150 amino acids, such as 40-1000, 50-900, 60-800, 70-700, 80-600, 90-500, 100-400 amino acids.

Standard amino acid nomenclature is used herein. Thus, the full name of an amino acid residue may be used interchangeably with one letter code or three letter abbreviations. For instance, lysine may be substituted with K or Lys, isoleucine may be substituted with I or Ile, and so on. Moreover, the terms aspartate and aspartic acid, and glutamate and glutamic acid are used interchangeably herein and may be replaced with Asp or D, or Glu or E, respectively.

As discussed above, the polypeptide of the present invention forms one part of a two-part affinity purification system and finds particular utility in purifying (i.e. isolating or separating) molecules or components (fusion partners) comprising (e.g. joined or conjugated to) a cognate peptide tag as defined herein.

Thus, in a further aspect, the invention may be seen to provide the use of a polypeptide of the invention defined above to purify or isolate a molecule or component comprising a cognate peptide tag as defined herein, e.g. a peptide tag having an amino acid sequence with at least 80% sequence identity to a sequence as set forth in one of SEQ ID NOs: 3-5, preferably wherein said peptide comprises an aspartic acid at a position equivalent to position 8 of SEQ ID NO: 3, position 7 of SEQ ID NO: 4 and position 10 of SEQ ID NO: 5.

Affinity purification systems typically utilise a capture molecule (e.g. receptor) immobilised on a solid substrate to facilitate the capture, washing and elution of the target ligand. Thus, the polypeptide of the invention may be immobilised (e.g. fused, conjugated or linked) to a solid substrate (i.e. a solid phase or solid support). It will be evident that this may be achieved in any convenient way. Alternatively viewed, the invention provides a solid support on which the polypeptide of the invention is immobilised.

The manner or means of immobilisation and the solid support may be selected, according to choice, from any number of immobilisation means and solid supports as are widely known in the art and described in the literature. Thus, the polypeptide of the invention may be directly bound to the support, for example via a domain or moiety of the polypeptide (e.g. chemically cross-linked). In some embodiments, the polypeptide may be bound indirectly by means of a linker group, or by an intermediary binding group(s) (e.g. by means of a biotin-streptavidin interaction). Thus, the polypeptide may be covalently or non-covalently linked to the solid support. In certain embodiments the polypeptide is immobilised on a solid substrate via a covalent bond.

The linkage may be a reversible (e.g. cleavable) or irreversible linkage. Thus, in some embodiments, the linkage may be cleaved enzymatically, chemically, or with light, e.g. the linkage may be a light-sensitive linkage.

Linking groups of interest may vary widely depending on the nature of the solid support. The linking group, when present, is in many embodiments biologically inert.

Many linking groups are known to those of skill in the art and find use in the invention. In representative embodiments, the linking group is generally at least about 50 daltons, usually at least about 100 daltons and may be as large as 1000 daltons or larger, for example up to 1000000 daltons if the linking group contains a spacer, but generally will not exceed about 500 daltons and usually will not exceed about 300 daltons. Generally, such linkers will comprise a spacer group terminated at either end with a reactive functionality capable of covalently bonding to the solid support.

Spacer groups of interest may include aliphatic and unsaturated hydrocarbon chains, spacers containing heteroatoms such as oxygen (ethers such as polyethylene glycol) or nitrogen (polyamines), peptides, carbohydrates, cyclic or acyclic systems that may possibly contain heteroatoms. Spacer groups may also be comprised of ligands that bind to metals such that the presence of a metal ion coordinates two or more ligands to form a complex. Specific spacer elements include: 1,4-diaminohexane, xylylenediamine, terephthalic acid, 3,6-dioxaoctanedioic acid, ethylenediamine-N,N-diacetic acid, 1,1'-ethylenebis(5-oxo-3-pyrrolidinecarboxylic acid), 4,4'-ethylenedipiperidine, oligoethylene glycol and polyethylene glycol. Potential reactive functionalities include nucleophilic functional groups (amines, alcohols, thiols, hydrazides), electrophilic functional groups (aldehydes, esters, vinyl ketones, epoxides, isocyanates, maleimides), functional groups capable of cycloaddition reactions, forming disulfide bonds, or binding to metals. Specific examples include primary and secondary amines, hydroxamic acids, N-hydroxysuccinimidyl esters, N-hydroxysuccinimidyl carbonates, oxycarbonylimidazoles, nitrophenylesters, trifluoroethyl esters, glycidyl ethers, vinylsulfones, and maleimides. Specific linker groups that may find use in the subject blocking reagent include heterofunctional compounds, such as azidobenzoyl hydrazide, N-[4-(p-azidosalicylamino)butyl]-3'-[2'-pyridyldithio]propionamide), bis-sulfosuccinimidyl suberate, dimethyladipimidate, disuccinimidyltartrate, N-maleimidobutyryloxysuccinimide ester, N-hydroxy sulfosuccinimidyl-4-azidobenzoate, N-succinimidyl [4-azidophenyl]-1,3'-dithiopropionate, N-succinimidyl [4-iodoacetyl] aminobenzoate, glutaraldehyde, and succinimidyl-4-[N-maleimidomethyl]cyclohexane-1-carboxylate, 3-(2-pyridyldithio)propionic acid N-hydroxysuccinimide ester (SPDP), 4-(N-maleimidomethyl)-cyclohexane-1-carboxylic acid N-hydroxysuccinimide ester (SMCC), and the like. For instance, a spacer may be formed with an azide reacting with an alkyne or formed with a tetrazine reacting with a trans-cyclooctene or a norbornene.

In some embodiments, a polypeptide may be provided with means for immobilisation (e.g. an affinity binding partner, e.g. biotin or a hapten, capable of binding to its binding partner, i.e. a cognate binding partner, e.g. streptavidin or an antibody) provided on the support. In some embodiments, the interaction between the polypeptide and the solid support must be robust enough to allow for washing and elution steps in the process defined below, i.e. the interaction between the polypeptide and solid support is not disrupted (significantly disrupted) by the washing or elution steps. For instance, it is preferred that with each washing and/or elution step, less than 5%, preferably less than 4, 3, 2, 1, 0.5 or 0.1% of the polypeptide of the invention is removed or eluted from the solid phase.

As mentioned above and discussed in detail in the Examples, the inventors have determined that the substitution of a serine residue with cysteine at position 51 of the mutated SpyCatcher sequence facilitated the coupling of the polypeptide of the invention to a solid support with minimal disruption to SpyTag binding and elution. Without wishing to be bound by theory, it is hypothesised that coupling the polypeptide of the invention to a solid support via the cysteine residue at position 51 of SEQ ID NO: 1 maximised accessibility of the polypeptide to its cognate peptide tag (i.e. SpyTag and variants thereof).

Thus, in some embodiments the polypeptide is immobilised on a solid substrate via a covalent bond between the cysteine at a position equivalent to position 51 of SEQ ID NO: 1. In a particular embodiment, the polypeptide comprises an amino acid sequence with at least 80% sequence identity to a sequence as set forth in SEQ ID NO: 1, wherein the amino acid sequence comprises cysteine at position 51 and the polypeptide is immobilised on a solid substrate via a covalent bond between said cysteine and the solid substrate, wherein the specified amino acid residue is at a position equivalent to the position in SEQ ID NO: 1. The covalent bond may be formed by reacting the thiol group on the cysteine residue with an appropriate reactive group on the solid substrate. Thus, in some embodiments, the solid substrate may comprise an iodoacetyl group, e.g. the solid substrate may be an iodoacetyl-activated substrate.

Whilst it may be advantageous to immobilise the polypeptide of the invention on a solid support via the cysteine residue at position 51 of SEQ ID NO: 1, this is not essential.

The solid support (phase or substrate) may be any of the well-known supports or matrices which are currently widely used or proposed for immobilisation, separation etc. These may take the form of particles (e.g. beads which may be magnetic, para-magnetic or non-magnetic), sheets, gels, filters, membranes, fibres, capillaries, slides, arrays or microtitre strips, tubes, plates or wells etc.

The support may be made of glass, silica, latex or a polymeric material, e.g. a polysaccharide polymer material, such as agarose (e.g. sepharose). Suitable are materials presenting a high surface area for binding of the polypeptide. Such supports may have an irregular surface and may be for example porous or particulate, e.g. particles, fibres, webs, sinters or sieves. Particulate materials, e.g. beads are useful due to their greater binding capacity, particularly polymeric beads.

Conveniently, a particulate solid support used according to the invention will comprise spherical beads. The size of the beads is not critical, but they may for example be of the order of diameter of at least about 1 µm and preferably at least about 2 µm, 5 µm, 10 µm or 20 µm and have a maximum diameter of preferably not more than about 500 µm, and e.g. not more than about 100 µm.

Monodisperse particles, that is those which are substantially uniform in size (e.g. size having a diameter standard deviation of less than 5%) have the advantage that they provide very uniform reproducibility of reaction. Representative monodisperse polymer particles may be produced by the technique described in U.S. Pat. No. 4,336,173.

However, to aid manipulation and separation, magnetic beads are advantageous. The term "magnetic" as used herein means that the support is capable of having a magnetic moment imparted to it when placed in a magnetic field, and thus is displaceable under the action of that field. In other words, a support comprising magnetic particles may readily be removed by magnetic aggregation, which provides a quick, simple and efficient way of separating the particles following the binding to the SpyTag variant.

In some embodiments, the solid support is a resin, preferably a thiol-reactive resin. As described in the Examples, the inventors have determined that the polypeptide advantageously may be stored under suitable conditions for long periods, e.g. months or years, without significant loss of activity. Thus, in some embodiments, it is preferred that the resin is also stable in long-term storage under suitable conditions, such as in 20% ethanol at temperatures between 0-10° C., such as about 4° C.

Whilst it is envisaged that the polypeptide of, and for use in, the invention may be produced recombinantly, and this is a preferred embodiment of the invention, it will be evident that it may be useful to modify one or more residues in the polypeptide to facilitate its immobilisation on a solid substrate and/or to improve the stability of the polypeptide. Thus, in some embodiments, the polypeptide of, or for use in, the invention may comprise unnatural or non-standard amino acids.

In some embodiments, the polypeptide of, or for use in, the invention may comprise one or more, e.g. at least 1, 2, 3, 4, 5 non-conventional amino acids, such as 10, 15, 20 or more non-conventional amino acids, i.e. amino acids which possess a side chain that is not coded for by the standard genetic code, termed herein "non-coded amino acids". Such amino acids are well known in the art, and may be selected from amino acids which are formed through metabolic processes such as ornithine or taurine, and/or artificially modified amino acids such as 9H-fluoren-9-ylmethoxycarbonyl (Fmoc), (tert)-(B)utyl (o)xy (c)arbonyl (Boc), 2,2,5,7,8-pentamethylchroman-6-sulphonyl (Pmc) protected amino acids, or amino acids having the benzyloxy-carbonyl (Z) group.

Examples of non-standard or structural analogue amino acids which may be used in the polypeptide of, and for use in, the invention are D amino acids, amide isosteres (such as N-methyl amide, retro-inverse amide, thioamide, thioester, phosphonate, ketomethylene, hydroxymethylene, fluorovinyl, (E)-vinyl, methyleneamino, methylenethio or alkane), L-N methylamino acids, D-α methylamino acids, D-N-methylamino acids. Further non-standard amino acids which may be used in the polypeptide of, and for use in, the invention are disclosed in Willis and Chin, Nat Chem. 2018; 10(8):831-837, in Table 1 of WO2018/189517 and WO2018/197854, all of which are herein incorporated by reference.

Thus, in a further aspect the invention provides a process for purifying or isolating a molecule or component comprising a peptide (i.e. a cognate peptide tag) having an amino acid sequence with at least 80% sequence identity to a sequence as set forth in SEQ ID NO: 3, 4 or 5, wherein said peptide comprises an aspartic acid at a position equivalent to position 8 of SEQ ID NO: 3, position 7 of SEQ ID NO: 4 or position 10 of SEQ ID NO: 5, said process comprising:

a) providing a solid substrate on which a polypeptide of the invention is immobilised;

b) providing a sample comprising said molecule or component;

c) contacting the solid substrate of a) with the sample of b) under conditions that enable said peptide to selectively bind to said polypeptide, thereby forming a non-covalent complex between said polypeptide immobilised on the solid substrate and molecule or component comprising said peptide;

d) washing the solid substrate with a buffer;

e) separating the molecule or component comprising the peptide from the polypeptide immobilised on the solid substrate.

The cognate peptide tag of the affinity purification system described herein may be fused or conjugated to other molecules or to other components or entities (i.e. fusion partners) to facilitate their purification prior to other downstream applications, e.g. reacting the cognate peptide tag with a SpyCatcher polypeptide (such as a polypeptide comprising an amino acid sequence as set forth in SEQ ID NO: 10 or 11). Such molecules or components (i.e. entities) may be a nucleic acid molecule, protein (e.g. an antibody), peptide, small-molecule organic compound, fluorophore, metal-ligand complex, polysaccharide, nanoparticle, nanotube, polymer, cell, organelle, vesicle, virus, virus-like particle or any combination of these.

Thus, process or use of the invention may be used for the purification or isolation of a nucleic acid molecule, protein (e.g. an antibody), peptide, small-molecule organic compound, fluorophore, metal-ligand complex, polysaccharide, nanoparticle, nanotube, polymer, cell, organelle, vesicle, virus, virus-like particle or any combination of these to which the cognate peptide tag is fused or conjugated.

The cell may be a prokaryotic or eukaryotic cell. In some embodiments the cell is a prokaryotic cell, e.g. a bacterial cell.

In some embodiments, the cognate peptide tag may be conjugated or fused to a compound or molecule which has a therapeutic or prophylactic effect, e.g. an antibiotic, antiviral, vaccine, antitumour agent, e.g. a radioactive compound or isotope, cytokines, toxins, oligonucleotides and nucleic acids encoding genes or nucleic acid vaccines.

In some embodiments, the cognate peptide tag may be conjugated or fused to a label, e.g. a radiolabel, a fluorescent label, luminescent label, a chromophore label as well as to substances and enzymes which generate a detectable substrate, e.g. horse radish peroxidase, luciferase or alkaline phosphatase. This detection may be applied in numerous assays where antibodies are conventionally used, including Western blotting/immunoblotting, histochemistry, enzyme-linked immunosorbent assay (ELISA), or flow cytometry (FACS) formats. Labels for magnetic resonance imaging, positron emission tomography probes and boron 10 for neutron capture therapy may also be conjugated to the peptide tag described herein. Particularly, the peptide tag may be fused or produced with another peptide and/or may be fused or produced with another protein.

In a particularly useful embodiment, the cognate peptide tag is fused or conjugated with another peptide or polypeptide. For instance, the cognate peptide tag may be produced as part of another peptide or polypeptide using recombinant techniques as discussed above, i.e. as a recombinant or synthetic protein or polypeptide. Thus, in some embodiments, the process or use of the invention may be used for the purification or isolation of a recombinant or synthetic protein or polypeptide comprising the cognate peptide tag described herein.

It will be evident that the cognate peptide tag defined herein may be fused to any protein or polypeptide. The protein may be derived or obtained from any suitable source. For instance, the protein may be in vitro translated or purified from biological and clinical samples, e.g. any cell or tissue sample of an organism (eukaryotic, prokaryotic), or any body fluid or preparation derived therefrom, as well as samples such as cell cultures, cell preparations, cell lysates etc. Proteins may be derived or obtained, e.g. purified from environmental samples, e.g. soil and water samples or food samples are also included. The samples may be freshly prepared or they may be prior-treated in any convenient way e.g. for storage.

As noted above, in a preferred embodiment, the protein may be produced recombinantly and thus the nucleic acid molecules encoding said proteins may be derived or obtained from any suitable source, e.g. any viral or cellular material, including all prokaryotic or eukaryotic cells, viruses, bacteriophages, mycoplasmas, protoplasts and organelles. Such biological material may thus comprise all types of mammalian and non-mammalian animal cells, plant cells, algae including blue-green algae, fungi, bacteria, protozoa, viruses etc. In some embodiments, the proteins may be synthetic proteins. For example, the peptide and polypeptide (proteins) disclosed herein may be produced by chemical synthesis, such as solid-phase peptide synthesis.

The terms "conjugating" or "linking" in the context of the present invention with respect to connecting the cognate peptide tag to molecules or components for purification or isolation in the process or use of the invention refers to joining said peptide tag to said molecules or components, e.g. proteins, via a covalent bond, particularly a peptide bond between the peptide tag and a polypeptide. With respect to connecting the polypeptide of the invention to a solid substrate, "conjugating" or "linking" refers to joining said polypeptide to said solid substrate, e.g. beads, via a covalent bond, particularly a thioether bond between the polypeptide and solid substrate.

The sample used in the process of the invention (i.e. comprising the molecule or component comprising the cognate peptide tag, e.g. recombinant protein) may be from any biological or clinical sample, e.g. any cell or tissue sample of an organism (eukaryotic, prokaryotic), or any body fluid or preparation derived therefrom, as well as samples such as cell cultures, cell preparations, cell lysates etc. The samples may be freshly prepared or they may be prior-treated in any convenient way e.g. for storage.

In some embodiments, the step of separating the molecule or component comprising the peptide from the polypeptide immobilised on the solid substrate may comprise subjecting the solid substrate to conditions suitable to disrupt the polypeptide:cognate peptide tag complex, i.e. to disrupt the non-covalent interaction between the polypeptide and the cognate peptide tag.

In some embodiments, conditions suitable to disrupt the polypeptide:cognate peptide tag complex comprise contacting said complex with a with a solution comprising imidazole (e.g. at least 1.0 M, e.g. 1.0-4.0 M, 1.0-3.0 M or 2.0-3.0 M, preferably about 2.5 M imidazole). Other conditions that may be suitable to disrupt the complex include contacting the solid substrate with a low pH solution or buffer (e.g. 0.1 M glycine pH 2.0 at 4° C.), subjecting said complex to elevated temperatures, e.g. at least 30, 35, 40 or 45° C., such as 30-65, 35-60, 40-55° C., and/or incubating said complex with a solution comprising a competitor (e.g. 100 µM to 2 mM of the cognate peptide tag as defined above (most preferably SEQ ID NO: 5), e.g. in TBS pH 8.0 at 25° C. for 4 hours). In some embodiments, the solid substrate may be subjected to these conditions repeatedly, e.g. 2, 3, 4, 5 or more times, in order to maximise the yield of the molecule or component to be purified. In some embodiments, it may be advantageous to use a combination of conditions to maximise the yield of the molecule or component to be purified, e.g. a first step using a solution comprising imidazole and a second step using a low pH solution or buffer. Any suitable combination of conditions may be used and is within the purview of the skilled person. In embodiments where competitive peptide elution is used, i.e. wherein the complex is incubated with a competitor, such as the cognate peptide tag, the elution step may be repeated multiple times, e.g. 2, 3, 4, 5 or more times.

A "low pH solution or buffer" may be viewed as any solution or buffer suitable for disrupting the non-covalent interaction between the polypeptide of the invention and its cognate peptide tag partner. In some embodiments, the low pH solution or buffer is an antibody elution buffer. In this respect, it is evident that the pH of the solution necessary to disrupt the interaction between the polypeptide of the invention and its cognate peptide tag partner may depend on the components in the solution. By way of example, antibody elution buffers may comprise or consist of 50 mM glycine pH 2.2-2.8 or 100 mM citric acid buffer pH 3.5-4.0. Thus, in some embodiments, the low pH solution or buffer has a pH of 4.0 or less, e.g. 3.9, 3.8, 3.7, 3.6, 3.5, 3.4, 3.3, 3.2, 3.1, 3.0 or less, e.g. about 1.5-3.5, 1.6-3.4, 1.7-3.3, 1.8-3.2, 1.9-3.1 or 2.0-3.0, such as about 2.2-2.8 or 2.5-2.7.

Preferably the conditions that are used to disrupt the polypeptide:cognate peptide tag complex are such that the cognate peptide tag can still be used in downstream applications, i.e. the conditions do not lead to irreversible loss of activity of the cognate peptide tag.

While the use of SpyTag peptides for affinity purification is particularly advantageous because it provides the purified molecule or component with downstream functionality (i.e. the ability to be conjugated to other molecules via Spy-Catcher), the inventors have shown that the process of invention may find utility in the purification or isolation of only the target molecule or component, i.e. without the peptide tag. This may be achieved by separating the target molecule or component from the polypeptide immobilised on the solid substrate through a cleavage reaction that cleaves the peptide tag from the target molecule or component. As demonstrated in the Examples below, this embodiment of the invention may result in the isolation of the target molecule or component at high purity.

Thus, in some embodiments, the step of separating the molecule or component comprising the peptide from the polypeptide immobilised on the solid substrate may comprise subjecting the solid substrate to conditions suitable to cleave the peptide tag from the molecule or component comprising the peptide tag, i.e. by on-resin tag cleavage. This may be accomplished incorporating (e.g. genetically encoding) a cleavage site which can be recognised by one or more proteases specific for that site between the peptide tag and the target molecule or component. Cleavage of the target molecule:peptide tag fusion at the cleavage site by the specific protease(s) releases the target molecule or component from the polypeptide:cognate peptide tag complex, leaving the peptide tag still bound to the polypeptide. Suitable proteases and their respective recognition sites are well known in the art, and any appropriate setup may be utilised in the present method.

Thus, in some embodiments, the molecule or component comprising the peptide tag contains a cleavage site between the peptide tag and molecule or component, e.g. a cleavage site linking the peptide tag and molecule or component. Alternatively viewed, the peptide tag is fused or conjugated to the molecule or component indirectly via a cleavable linker. In some embodiments, the cleavage site or cleavable linker is a protease cleavage site, such as a TEV recognition site (e.g. SEQ ID NO: 26). Thus, in some embodiments, the step of separating the molecule or component comprising the peptide from the polypeptide immobilised on the solid substrate may comprise contacting the solid substrate with an entity (e.g. protease, e.g. SuperTEV) under conditions suitable to cleave the cleavage site or cleavable linker thereby releasing the molecule or component from the peptide tag and the polypeptide immobilised on the solid substrate.

The step of washing the solid substrate with a buffer prior to separating said complex from the solid substrate may utilise any suitable buffer, e.g. TBS. The buffer may be selected based on the molecules or components conjugated or linked to the peptide tag. Furthermore, the step of washing the solid substrate may be repeated multiple times, e.g. 2, 3, 4, 5 or more times. Alternatively viewed, in some embodiments the process comprises multiple wash steps, wherein the same or different washing conditions may be used in each step.

Where the solid substrate comprises beads (e.g. agarose-based beads) the volume of buffer used in the wash steps may be at least about 2 times the volume of the beads, e.g. at least about 3, 4, 5, 6, 7, 8, 9 or 10 times the volume of the beads.

In some embodiments, the solid substrate is subjected to stringent washing conditions. The nature of the stringent washing conditions will depend on the molecules or components conjugated or linked to the peptide tags and/or the composition of the solid substrate. The skilled person could select such conditions as a matter of routine. However, by way of example, stringent washing conditions may comprise washing with a buffer (e.g. TBS) comprising about 300-700 mM imidazole, preferably about 400-600 mM imidazole (e.g. about 500 mM imidazole), wherein each wash may be repeated.

The temperature of the washing and separation (elution) steps may be determined readily by a person of skill in the art based on routine experimentation and may depend on the nature of the molecule or component being isolated or purified. In some embodiments, the washing and/or separation steps are performed at 10° C. or less, e.g. 9, 8, 7, 6, 5 or 4° C. or less.

Whilst it may be useful to immobilise the polypeptide of the invention on a solid support prior to contact with the sample comprising the molecule or component comprising the cognate peptide tag, it will be evident that this is not essential. For instance, the binding of the polypeptide of the invention and the component comprising the cognate peptide tag may take place in solution, which is subsequently applied to a solid support or solid phase, e.g. column, for subsequent washing and separation (e.g. elution) steps. In some embodiments, the polypeptide:cognate peptide tag complex may be applied to the solid phase under conditions suitable to immobilise the complex on the solid phase via the polypeptide (e.g. an immobilisation domain on the polypeptide), washed under suitable conditions and subsequently subjected to one or more of the conditions mentioned above, e.g. contacted with a solution comprising imidazole, to disrupt the complex, thereby separating the polypeptide and the component comprising the cognate peptide tag.

As described in the Examples below, the inventors have shown that once the molecule or component comprising the cognate peptide tag has been separated from the immobilised polypeptide, the solid support comprising the polypeptide may be reused, e.g. for further purification reactions. In some embodiments, the solid support comprising the polypeptide may be subject to a regeneration process, to ensure that all of the component or molecule comprising the peptide tag has been removed, before it is reused. This regeneration process may involve repeated washes under conditions suitable to remove any residual peptide tags and/or peptide tag complexes. For example, the solid support comprising the polypeptide may be subjected to washes of imidazole, guanidine hydrochloride (GuHCl) and/or NaOH. In some embodiments, the solid support comprising the polypeptide may be subjected to consecutive treatments of about 4 M imidazole (e.g. in Tris-phosphate at pH 7.0), about 6 M GuHCl at about pH 2.0 and about 0.1 M NaOH, optionally with a physiological wash (e.g. using a wash buffer as described above) in between each treatment condition.

In a further aspect, the invention provides an apparatus for use in the process or use hereinbefore defined comprising a solid substrate on which a polypeptide of the invention is immobilised.

In some embodiments, the apparatus may comprise a chromatography column comprising the solid substrate on which a polypeptide of the invention is immobilised. The apparatus may further comprise means for contacting the solid substrate with the sample, washing and elution buffers and/or means for removing (e.g. aspirating) or collecting liquids (e.g. wash-through, eluted fractions) from the solid substrate.

In a further aspect, the invention provides a kit, particularly a kit for use in preparing a solid substrate on which a polypeptide of the invention is immobilised, comprising:
 a) a polypeptide of the invention; and
 b) means for immobilising the polypeptide of a) on a solid substrate.

In a further embodiment, the kit further comprises a solid substrate as defined above.

Means for immobilising the polypeptide of the invention on a solid substrate may comprise reagents for activating the solid substrate (e.g. resin) and/or polypeptide (e.g. tris(2-carboxyethyl)phosphine), reagents for coupling the polypeptide to the solid substrate (e.g. coupling buffer, such as 50 mM Tris-HCl, 5 mM EDTA, pH 8.5) and/or reagents for blocking the solid substrate (e.g. L-cysteine-HCl in coupling buffer).

The invention will now be described in more detail in the following non-limiting Examples with reference to the following drawings:

FIG. 1 shows a cartoon of the Spy&Go purification process involving SpyDock coupled to resin beads via an anchoring mutation to enable the solid-phase purification of SpyTag-fused proteins, including several potential uses for the SpyTag-Protein complex following purification involving multimerization on SpyCatcher-based platforms FIG. 2 shows an SDS-PAGE gel with Coomassie staining showing the results of an experiment wherein a SpyTag-MBP fusion protein was incubated for 24 hours with a SpyCatcher polypeptide or mutants SEQ ID NO: 13 (EA) and SEQ ID NO: 12 (ED), and demonstrates that the E79A mutation (EA) prevents a covalent reaction between SpyCatcher and SpyTag.

FIG. 3 shows SDS-PAGE gels depicting the purification of a SpyTag-MBP fusion protein from a bacterial expression system. SpyTag-MBP doped into E. coli clarified lysate was purified (A) by Spy&Go; and (B) by Ni-NTA via a His-tag. The fractions were analyzed by SDS-PAGE with Coomassie staining. Purity of total pooled elution was determined by densitometry (right); "Lysate" is the clarified cell lysate; "Protein" is the input SpyTag-MBP; "Lysate+Protein" is cell lysate mixed with SpyTag-MBP; "Flow-through" is flow-through from resin binding; "Wash" is total washes with 500 mM imidazole in Tris-phosphate buffer pH 7.0; Elution fractions "1-4" with 2.5 M imidazole in Tris-phosphate buffer pH 7.0; Elution "T" represents total pooled elutions; "Resin" is polypeptide from the resin post-elution.

FIG. 4 shows SDS-PAGE gels depicting the purification of a fusion protein comprising extracellular region of EpCAM fused to SpyTag and a His-tag (EpCAM-SpyTag) from a mammalian expression system. EpCAM-SpyTag was purified from the clarified cell supernatant using (A) Spy&Go or (B) Ni-NTA purification. Fractions were analyzed by SDS-PAGE with Coomassie staining. Purity of total pooled elution was determined by densitometry (right). "Supernatant" represents HEK293T supernatant post-expression; "Flow-through" represents flow-through from resin binding; "Wash" represents total washes with Tris-phosphate pH 7.0; Elution fractions "1-6" with 2.5 M imidazole in Tris-phosphate pH 7.0; Elution "T" represents total pooled elutions; "Resin" represents polypeptide from the resin post-elution.

FIG. 5 shows an SDS-PAGE gel with Coomassie staining depicting the results of an experiment involving SpyTag-MBP and a number of unreactive SpyCatcher variants comprising different mutations at residue 79. These mutants were incubated with SpyTag-MBP for 24 hours to assess the interaction between the pair, and particularly to investigate any potential covalent bond formation.

The mutants constructed are outlined in the table below.

TABLE 1

| SEQ ID NO: | Label in figures |
|---|---|
| 6 | A |
| 23 | D |
| 14 | G |
| 15 | N |
| 16 | Q |
| 17 | S |
| 18 | T |
| 19 | V |
| 20 | E79A K30A |
| 21 | SpyCatcher E79A |
| 22 | SpyCatcher002 E79A |
| 7 | SpyCatcherΔN1 E79A |

FIG. 6 shows an SDS-PAGE gel depicting relative efficiency of the purification of SpyTag-MBP using the unreactive SpyCatcher mutants in Table 1 linked to resin columns. Pure SpyTag-MBP was incubated with each of the mutant SpyCatcher resins for 1 hour before being washed and eluted. The elution fractions for each mutant were pooled and analyzed by SDS-PAGE with Coomassie staining.

Figure 9:
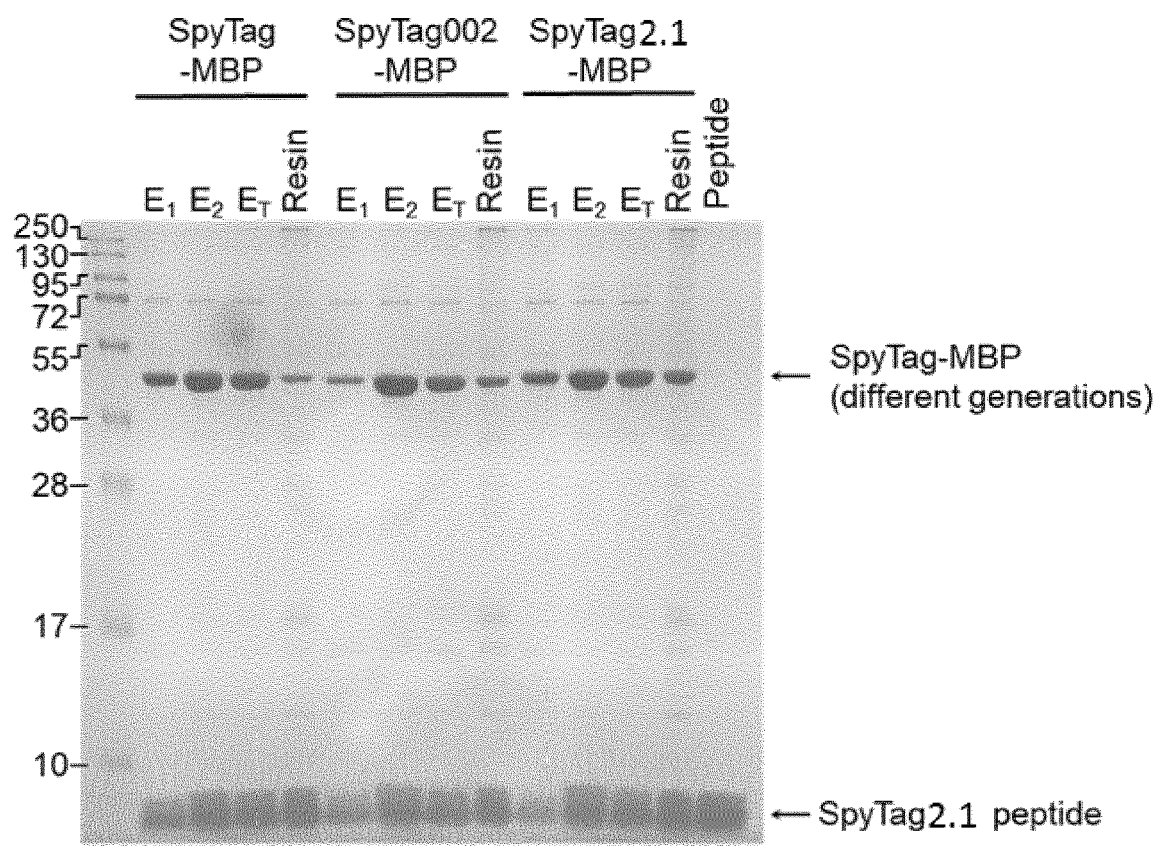

FIG. 9 shows an SDS-PAGE gel with Coomassie staining depicting competitive peptide elution of different SpyTag-MBP generations from Spy&Go resin (i.e. SpyDock linked to resin). 1 mM of SpyTag2.1 peptide in Tris-phosphate buffer pH 7.0 was incubated with Spy&Go resin bound with SpyTag-, SpyTag002-, or SpyTag2.1-MBP spiked into E. coli lysate and washed. The incubation was done for 2×2 hours at 30° C. E1: first elution, E2: second elution, ET: total pooled elution, and Resin: boiled resin fraction.

Figure 10:
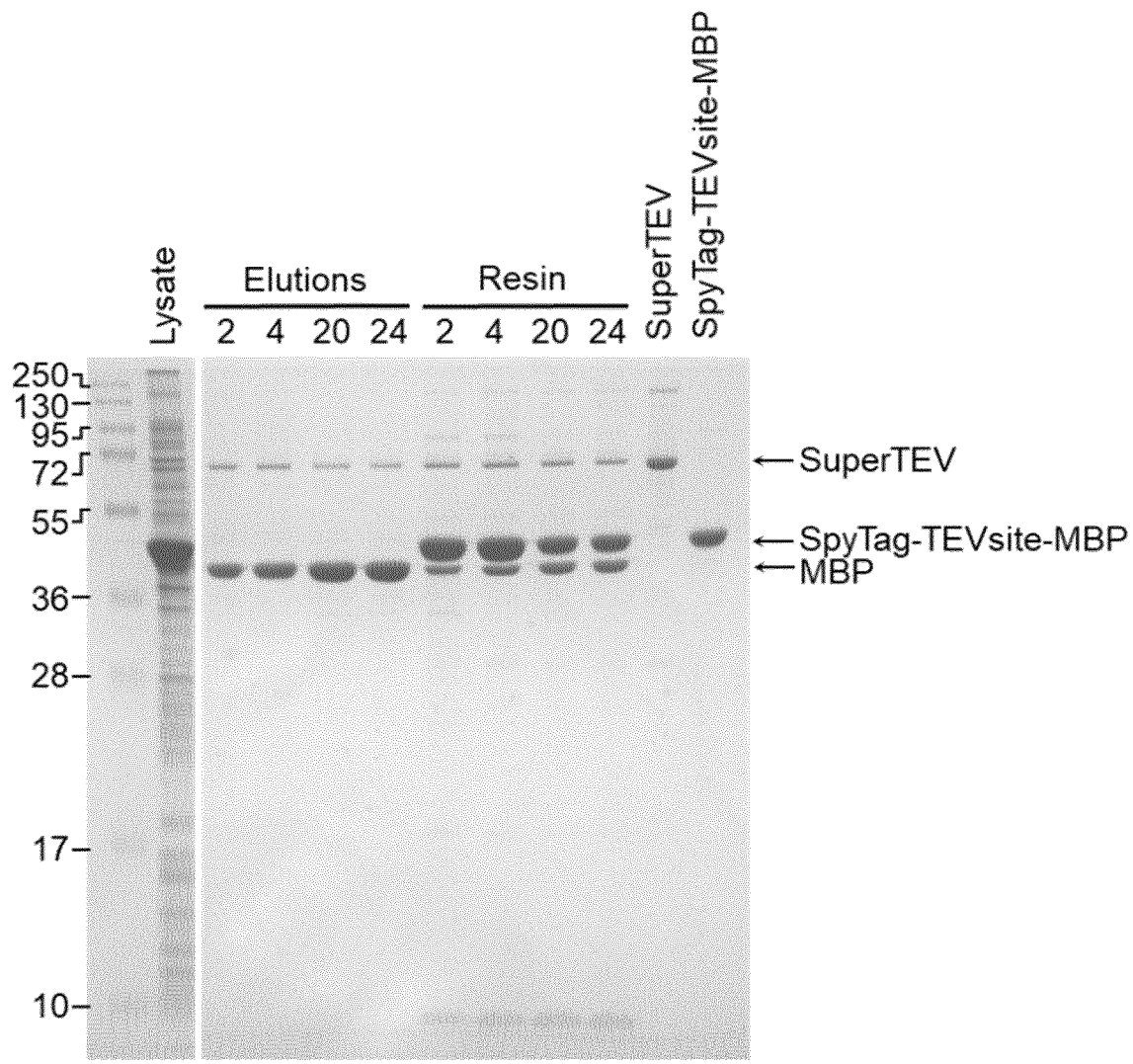

FIG. 10 shows an SDS-PAGE gel with Coomassie staining depicting on-resin tag cleavage of SpyTag-TEVsite-MBP using SuperTEV protease. Recombinant SpyTag-TEVsite-MBP was incubated with Spy&Go resin and washed. MBP was eluted by incubating with 0.5 mg/mL of Super-TEV protease for 2, 4, 20, or 24 hours at 4° C. The elution and resin fractions were loaded SDS-PAGE gel and Coomassie-stained. Controls of SuperTEV and SpyTag-TEVsite-MBP were shown for size comparison.

Figure 11:
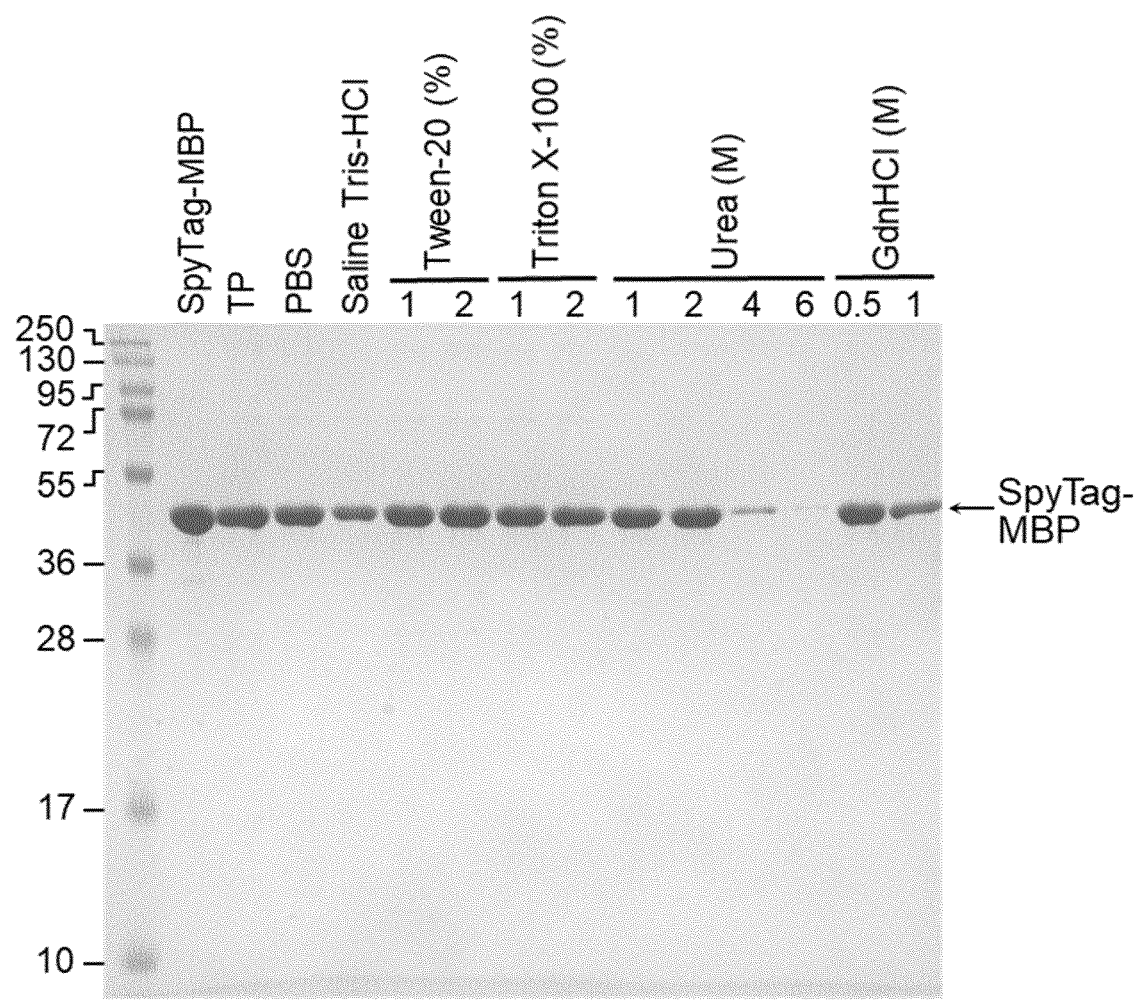

FIG. 11 shows an SDS-PAGE gel with Coomassie staining depicting the binding buffer capability of Spy&Go resin. Purified SpyTag-MBP was incubated with Spy&Go resin in the different binding buffers, washed with 500 mM imidazole in Tris-phosphate pH 7.0, and eluted with 2.5 M imidazole in Tris-phosphate pH 7.0. Total pooled elution fractions were loaded onto a non-reducing SDS-PAGE gel and stained with Coomassie staining for comparison of binding buffer compatibility.

Figure 12:
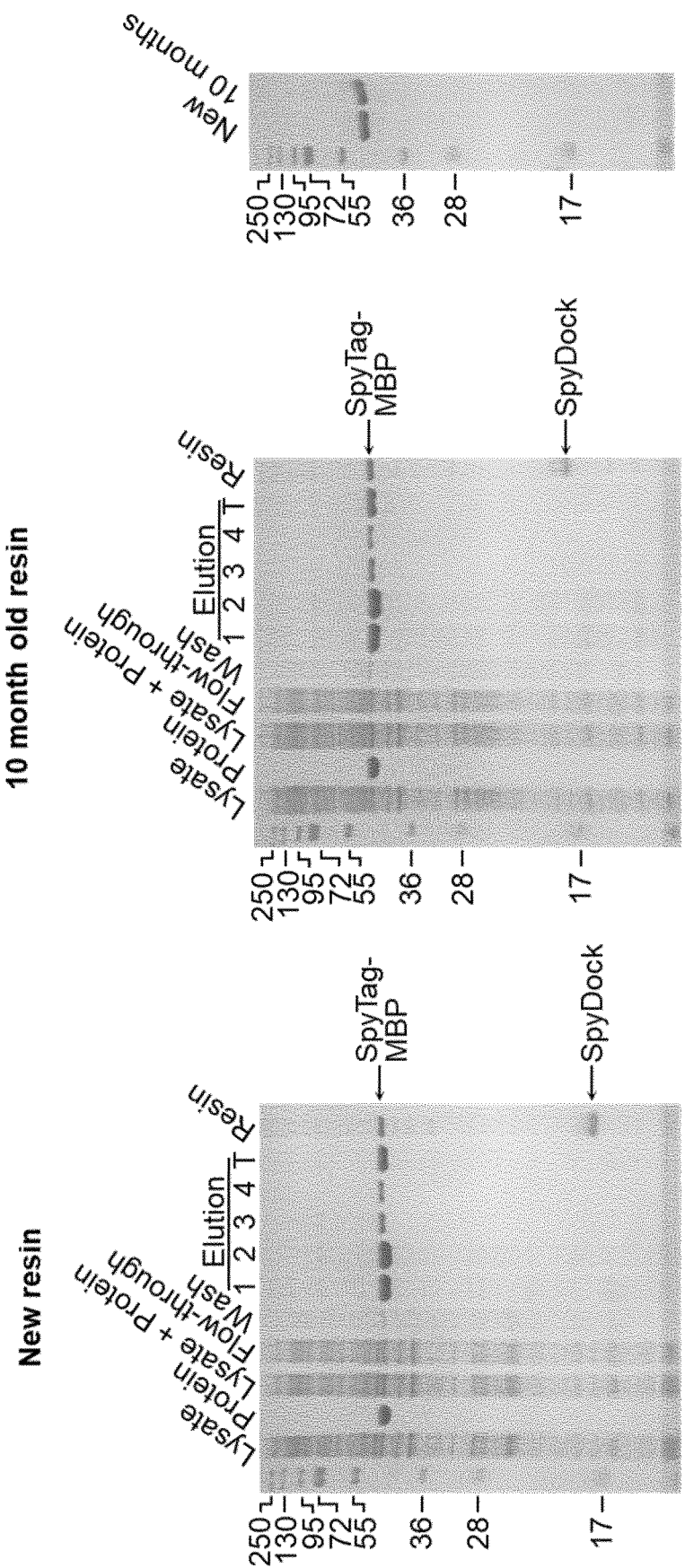

FIG. 12 shows SDS-PAGE gels with Coomassie staining depicting the ability to purify SpyTag-MBP of new Spy&Go resin (left), and Spy&Go resin following storage in 20% ethanol for 10 months (centre). A direct comparison is shown on the gel on the right. SpyTag-MBP was spiked into E. coli cell lysate and mixed with immobilised SpyDock, washed with 500 mM imidazole in Tris-phosphate pH 7.0, and eluted with 2.5 M imidazole in Tris-phosphate pH 7.0. Total pooled elution fractions were loaded onto a non-reducing SDS-PAGE gel and stained with Coomassie staining. No difference in purification quality and capacity was observed. T: total pooled elutions.

Figure 13:
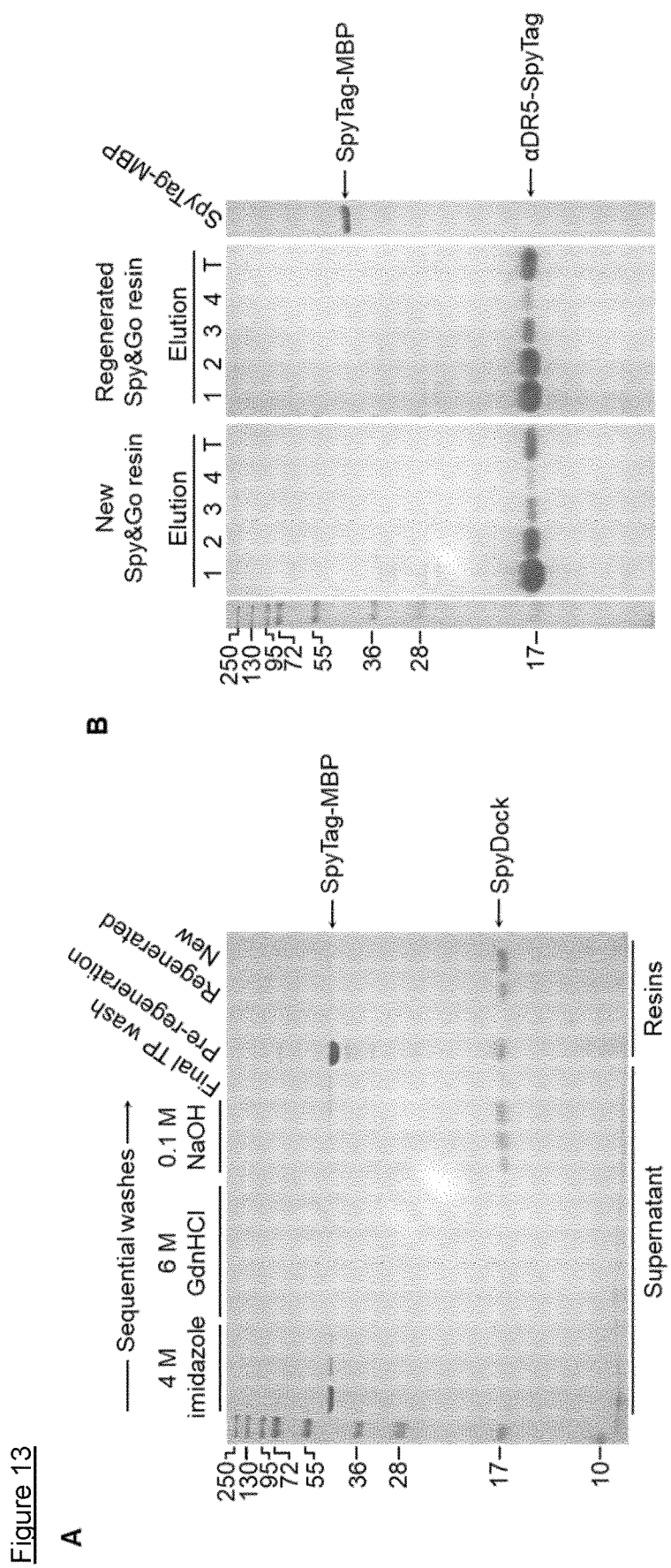

FIG. 13 shows SDS-PAGE gels with Coomassie staining depicting the ability of Spy&Go resin to be regenerated and reused. (A) shows the results of regeneration steps to remove residual SpyTag-MBP from a previous purification. "Pre-regeneration" is the resin after the initial SpyTag-MBP purification. "Regenerated" is the resin following sequential imidazole, guanidinium hydrochloride and NaOH washes, in comparison to a "New" unused resin batch. (B) shows subsequent purification of αDR5-SpyTag using new unused Spy&Go resin or regenerated Spy&Go resin from (A). Elution fractions 1-4 and the total pooled elution (T) fraction are shown.

EXAMPLES

Example 1—Mutation of SpyCatcher002 (SEQ ID NO: 11)

As a first step to establish an affinity partner for SpyTag, it was necessary to abrogate the formation of an isopeptide bond between SpyCatcher polypeptides and SpyTag, to make possible the elution of SpyTag-fusions. It was also hypothesised that further modifications to the SpyCatcher002 sequence may be required to enhance the interaction between SpyCatcher002 and SpyTag peptides in order to generate an affinity partner for SpyTag.

To complement the positively charged residues of the SpyTag variant set forth in SEQ ID NO: 5, the glutamine residue at position 99 of SEQ ID NO: 11 was mutated to aspartic acid to improve electrostatic interactions with the N-terminal arginine of SEQ ID NO: 5. Similarly, the lysine residue at position 110 of SEQ ID NO: 11 was mutated to glutamic acid to improve the interaction with the C-terminal arginine and lysine residues of the SpyTag variant (SEQ ID NO: 5). The alanine residue at position 91 of SEQ ID NO: 11 was mutated to proline on the basis that introducing proline turns and loops can stabilize proteins.

In order to generate a non-reactive "pseudo-SpyCatcher", the activating glutamic acid residue in the SpyCatcher variant described above, E79, was mutated either to aspartic acid (SEQ ID NO: 12) to retain the charge or to alanine (SEQ ID NO: 13) to stop proton donation/acceptance. The SpyCatcher variants were mixed with 4 µM SpyTag-MBP at 25° C. for 24 h in PBS.

Figure 1:
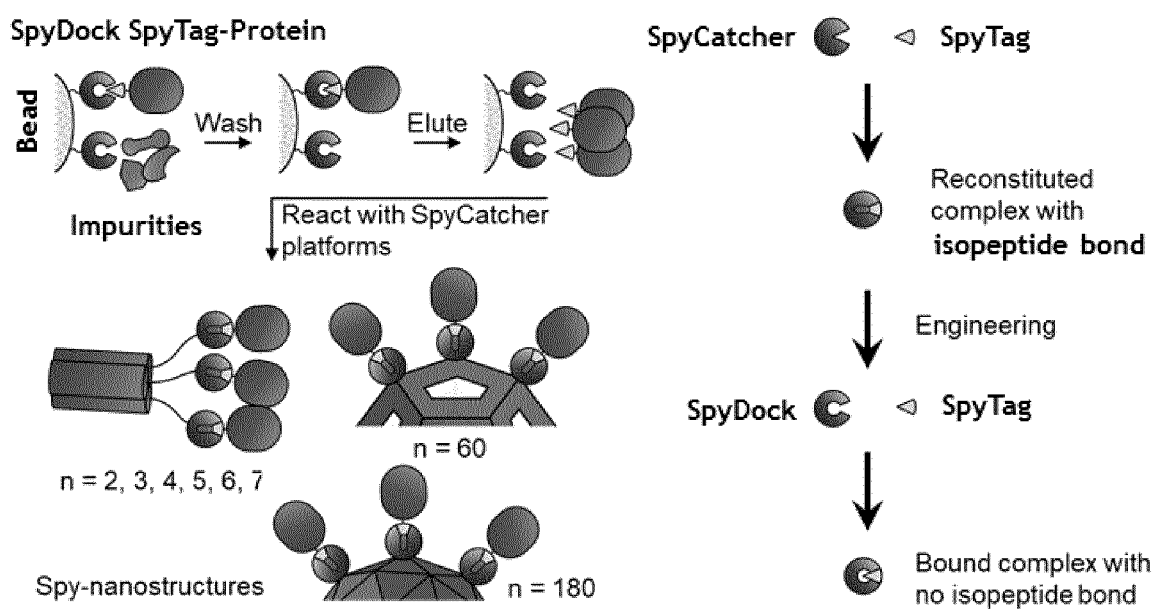
Figure 2:
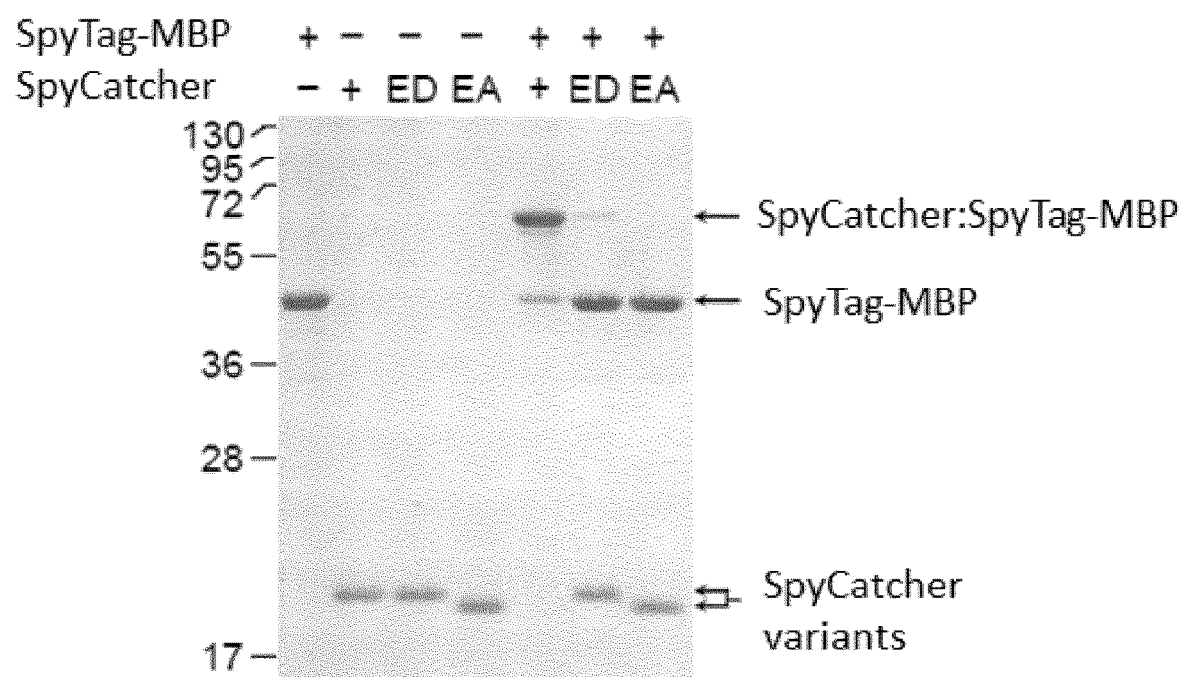

SEQ ID NO: 12 still showed a small amount of reaction with SpyTag-MBP, but no trace of reaction was seen with SEQ ID NO: 13 (FIG. 2). Therefore, unreactive "pseudo"-SpyCatcher set forth in SEQ ID NO: 13 was taken forward to subsequent development.

Example 2—Coupling the Unreactive "Pseudo"-SpyCatcher (SEQ ID NO: 13) to Resin

Purified unreactive "pseudo"-SpyCatcher (SEQ ID NO: 13) was modified to contain various cysteine anchoring residues (N-term Cys (SEQ ID NO: 24), S57C (SEQ ID NO: 25), and S51C (SEQ ID NO: 6)) and was conjugated to SulfoLink Coupling Resin (Thermo Fisher Scientific) according to the manufacturer's protocol. In short, 20 mg of protein for every 1 mL of resin was reduced by 1 mM tris(2-carboxyethyl)phosphine (TCEP-HCl) (Fluorochem) for 30 min, prior to mixing with equilibrated resin for 15 min, and left to stand for 30 min covered by foil. Protein flow-through was aspirated, resin washed with 10 resin volumes of coupling buffer (50 mM Tris-HCl, 5 mM EDTA, pH 8.5) and blocked with 50 mM L-cysteine-HCl in coupling buffer (MP Biomedicals). The sample was mixed for 15 min and left to stand for 30 min. The resin was then washed with 10 resin volumes of 1 M NaCl and stored in Tris-phosphate buffer (25 mM orthophosphoric acid adjusted to pH 7.0 with Tris base) with 0.05% (v/v) $NaN_3$ at 4° C.

For an initial test to determine the best cysteine anchoring site, 50 μL packed resin with one of SEQ ID NOs: 24, 25 or 6 were mixed with 500 μL Tris-phosphate buffer containing 0.09 mg Ni-NTA-purified SpyTag-MBP in an Eppendorf tube through batch chromatography. The low amount of SpyTag-MBP introduced was to test the sensitivity of purification. The SpyTag-MBP protein was mixed with the resin for 1 h with tumbling at 4° C. For standard batch chromatography purification, the resin was washed 4× with 10 resin volumes of Tris-phosphate buffer, with incubation at 4° C., shaking at 1,200 rpm for 3 min, and centrifugation at 4,000 g for 3 min at 4° C. The protein was eluted with 4×1.5 resin volumes of elution buffer (2.5 M imidazole in Tris-phosphate buffer pH 7.0).

Figure 7:
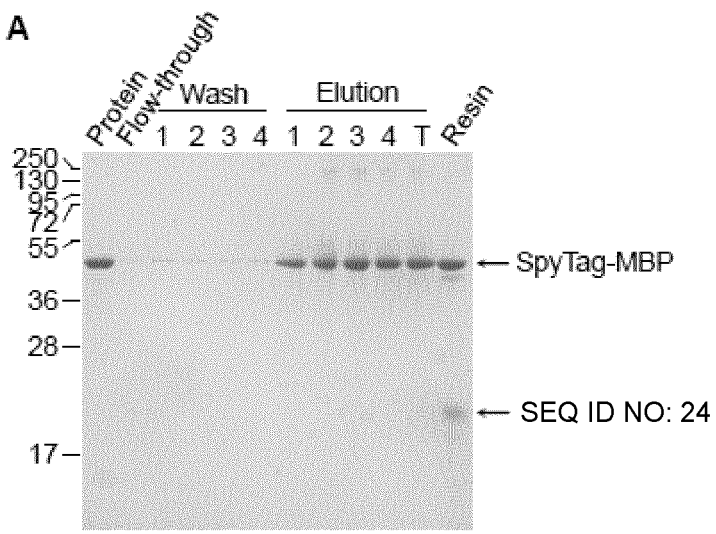
FIG. 7 shows SDS-PAGE gels with Coomassie staining depicting relative efficiency of the purification of SpyTag-MBP using SpyDock variants linked to resin columns by cysteine-anchoring residues at different positions, wherein: A) shows purification using SEQ ID NO: 24; B) shows purification using SEQ ID NO: 6; and C) shows purification using SEQ ID NO: 25.
Figure 7:
Figure 7:
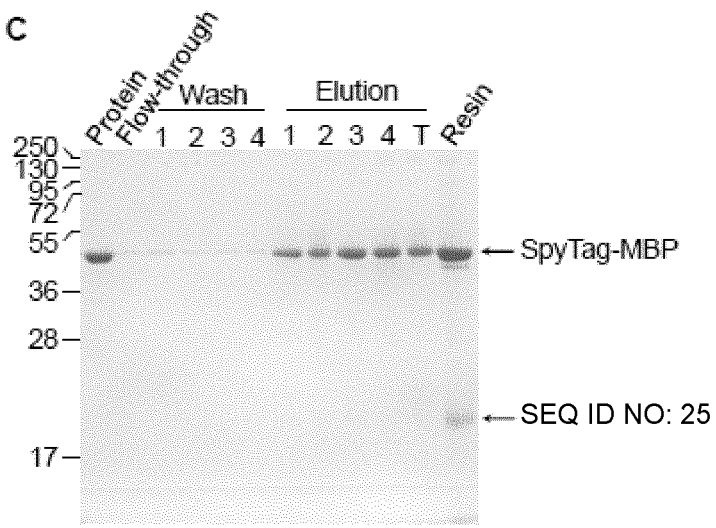

It was found that high concentrations of imidazole were the most efficient elution buffer, which has been shown to be well tolerated by different proteins. All Cys mutants showed similar SpyTag-MBP retention and minimal leak-through during washes, but SEQ ID NO: 6 had the least SpyTag-MBP retained on the resin after elution (see FIG. 7). The polypeptide sequence set forth in SEQ ID NO: 6 was termed "SpyDock".

Example 3—SpyTag ("Spy&Go") Purification from Bacterial Expression pET28a-SpyTag-MBP was transformed into chemically-competent *E. coli* BL21 (DE3) RIPL (Agilent Technologies). A pDEST14-SpyDock fusion was transformed into chemically-competent *E. coli* C41 (DE3), a kind gift from Anthony Watts (University of Oxford). The cells were plated on LB agar supplemented with 50 μg/mL kanamycin (pET28a) or 100 μg/mL ampicillin (pDEST14). The plates were incubated at 37° C. overnight until colonies were observed.

Single colonies of pET28a-SpyTag-MBP, and pDEST14-SpyDock were picked and inoculated into 10 mL LB medium supplemented with 50 μg/mL kanamycin (pET28a) or 100 μg/mL ampicillin (pDEST14). Cells were incubated at 37° C. with shaking at 200 rpm for 16 h. Cultures of pET28a-SpyTag-MBP and pDEST14-SpyDock were then inoculated into 1 L LB supplemented with 50 μg/mL kanamycin (pET28a) or 100 μg/mL ampicillin (pDEST14) and 0.8% glucose. Cells were incubated at 37° C. with shaking at 200 rpm until A600 0.5-0.6, when the cultures were induced with 0.42 mM isopropyl β-D-1-thiogalactopyranoside (IPTG) (Fluorochem). Cultures of pET28a-SpyTag-MBP and pDEST14-SpyDock were grown further for 4 h with shaking at 200 rpm at 30° C.

For purification of SpyTag-MBP from lysate, 0.09 mg of the Ni-NTA-purified proteins were added into 0.25 g wet cell weight of induced BL21 (DE3) RIPL cleared lysate resuspended in 500 μL Tris-phosphate buffer with 50 μL packed SpyDock resin. The protein-lysate was mixed with the resin for 1 h with tumbling at 4° C. Standard Spy&Go batch chromatography purification (described above) was performed to purify the proteins but washed with 500 mM imidazole in Tris-phosphate buffer pH 7.0.

For comparison with Ni-NTA resin, the methods described above were performed with equivalent volume of packed Ni-NTA resin with the following changes: the cell pellet was resuspended in 50 mM Tris-HCl, 300 mM NaCl pH 7.8, the wash buffer was Ni-NTA wash buffer and elution buffer was Ni-NTA elution buffer.

Figure 3:
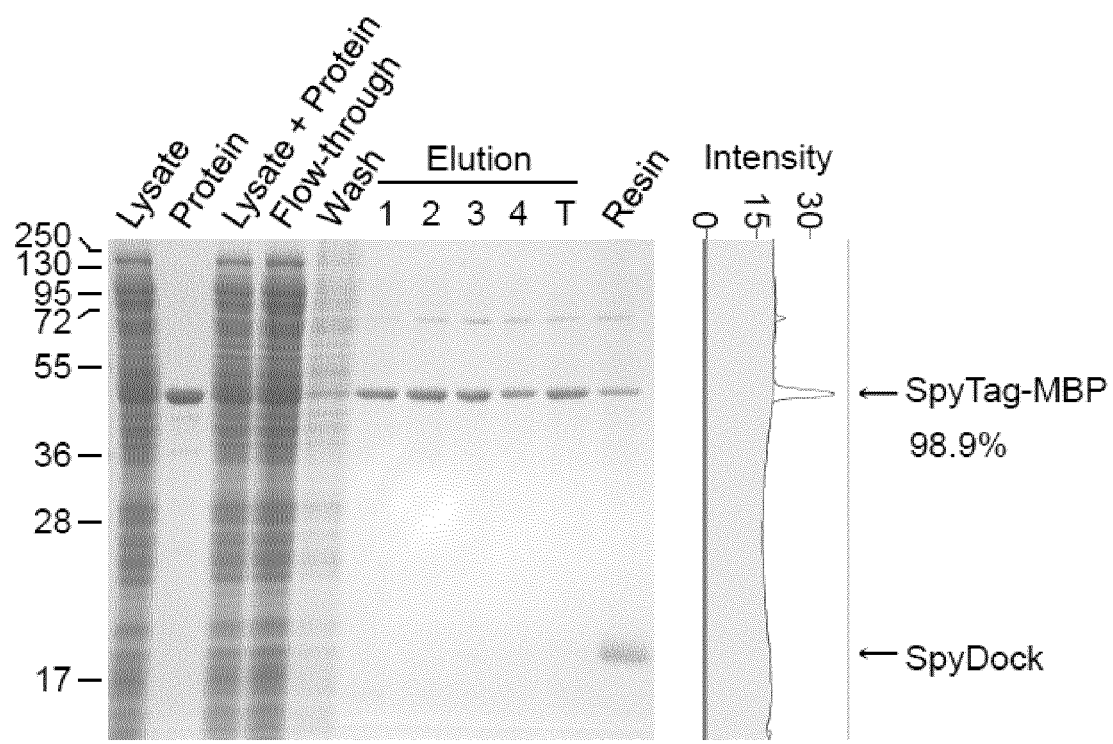
Figure 3:
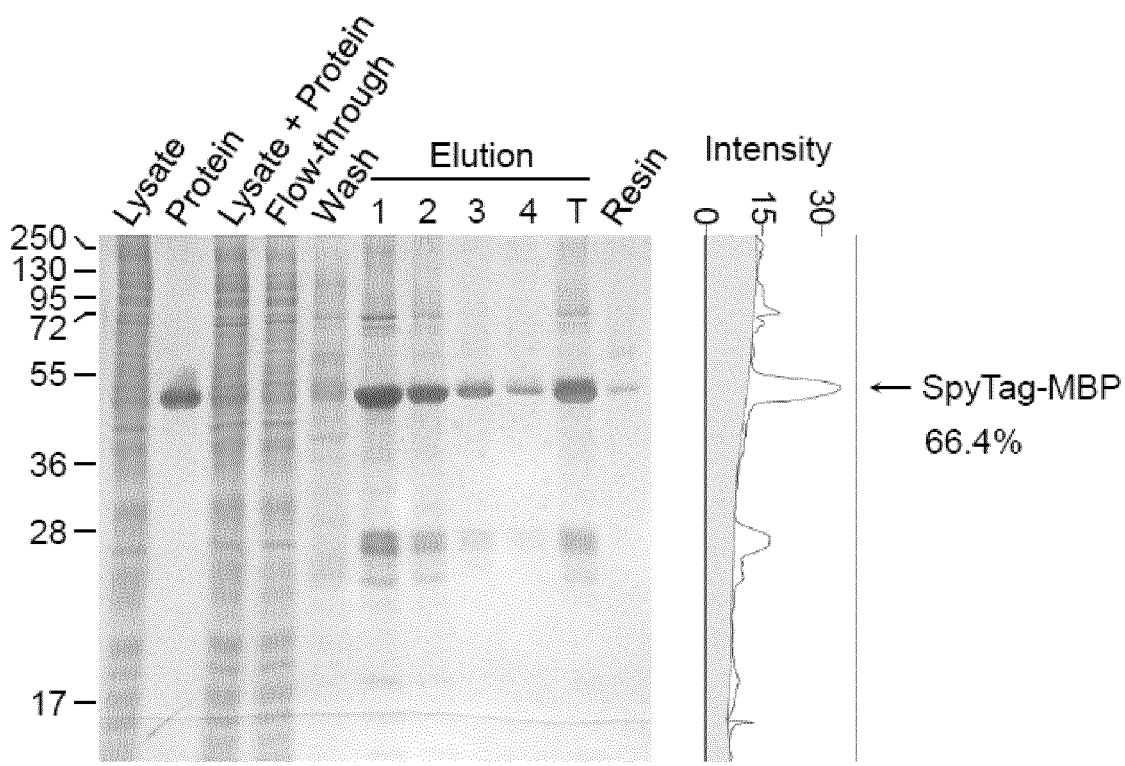
Figure 8:
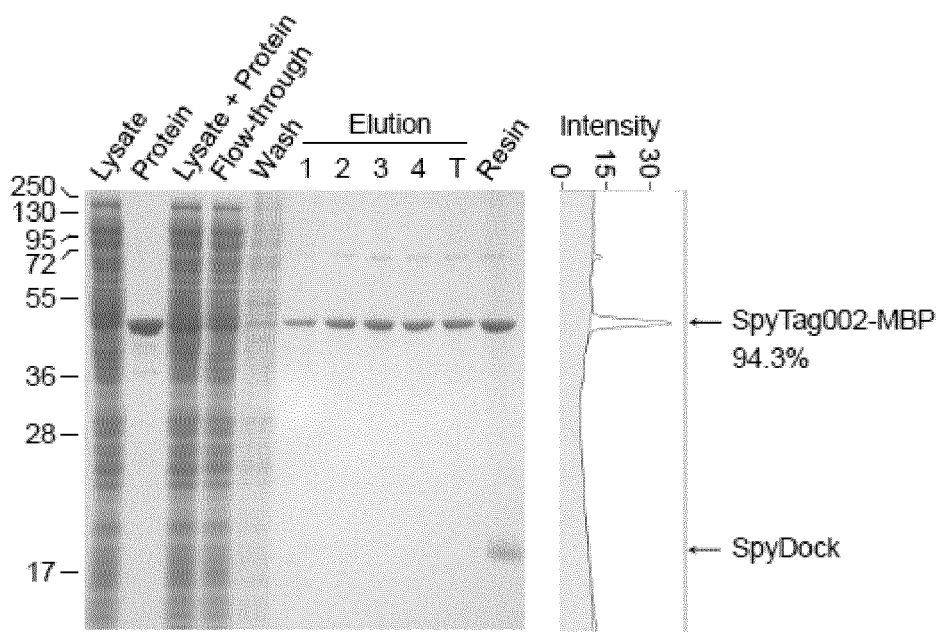
FIG. 8 shows SDS-PAGE gels with Coomassie staining depicting relative efficiency of the purification of SpyTag-MBP variants using SpyDock linked to resin columns, wherein: A shows the purification of SpyTag002-MBP: and B) shows the purification of SpyTag2.1-MBP.
Figure 8:
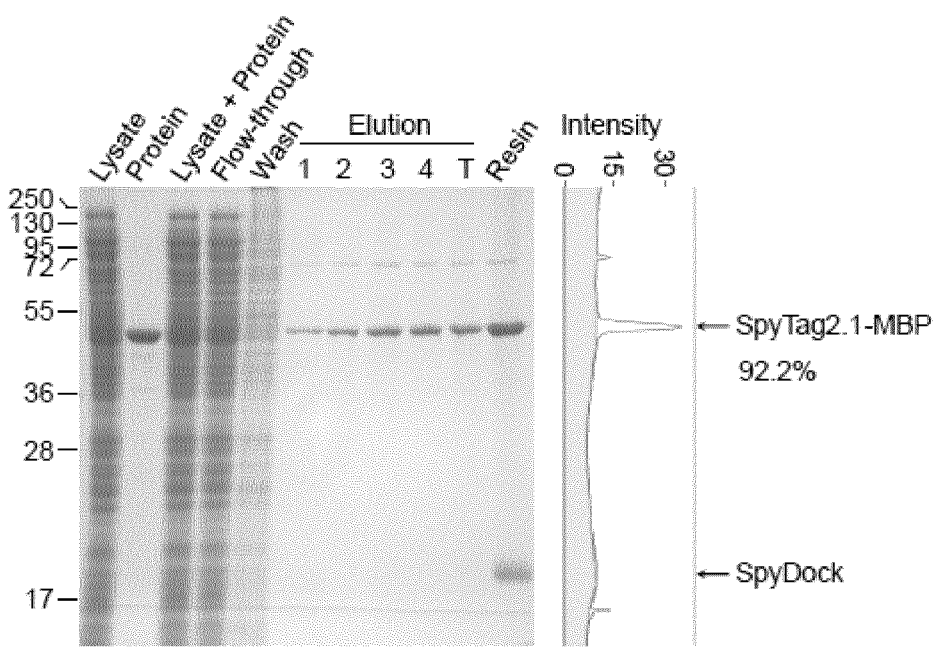

The capability of the affinity purification system of the invention (SEQ ID NO: 6 coupled to resin) was evaluated for purification of proteins from cellular material. Affinity purification becomes easier when proteins are highly overexpressed, so the system was challenged by doping a low amount of purified SpyTag-MBP into clarified *E. coli* lysate at 0.36 mg protein per g of wet cell weight. For context, ~5 mg of protein per g of wet cell weight is usually obtained. A series of optimizations established that imidazole was efficient at eluting SpyTag-MBP from SpyDock, with lower imidazole concentrations used in the wash buffer. As a bench mark for Spy&Go purification, the SpyTag protein also had a His6-tag, so that the same protein and lysate could be compared for the common approach of Ni-NTA purification. The same amount of His-tagged SpyTag-MBP in clarified *E. coli* lysate was mixed with Ni-NTA resin at the same volume. Spy&Go-based purification enabled purification of SpyTag-MBP with higher purity (98.9%) than via Ni-NTA purification (66.4%) (FIG. 3). SpyTag (SEQ ID NO: 4) is the most widely used partner of SpyCatcher in the literature so our purification approaches focused on the parental tag version. However, we also validated that Spy&Go purification was efficient with the recent SpyTag variants, SpyTag002 (SEQ ID NO: 3) and SpyTag2.1 (SEQ ID NO: 5), although a higher elution volume is recommended (FIG. 8).

Example 4—Spy&go Purification from Mammalian Expression

The purification of a C-terminally-tagged protein from mammalian cell culture was also tested. The soluble extracellular region of Epithelial Cell Adhesion Molecule (EpCAM) was tagged with both SpyTag and His-tag at the C-terminus and expressed through transient transfection in HEK293T cells.

HEK293T cells were cultured in T175 adhesive culture flasks (Corning) with Dulbecco's Modified Eagle's Medium (DMEM) (Sigma-Aldrich) high glucose with 10% (v/v) Fetal Bovine Serum (Sigma-Aldrich), 2 mM L-glutamine, 100 U/mL penicillin, and 100 μg/mL streptomycin (Thermo Fisher Scientific) at 37° C. with 5% $CO_2$. Before transfection, the cells were seeded into a T875 5-layer flask (Corning) and upon reaching 50% confluency, the cells were transferred into serum-free media (DMEM, 2 mM glutamine, 100 U/mL penicillin, 100 μg/mL streptomycin with 25 mM HEPES added) and mixed with 4 μg/mL pENTR4-EpCAM-SpyTag plasmid per 7.5 mL of media for each flask layer. After 15 min, 2.5 mL media containing 36 μg/mL polyethyleneimine (Sigma-Aldrich) was added to each layer. 10 mL media containing 4.4 μM valproic acid (Sigma-Aldrich) was added to each layer 16-20 h later. Cells were then incubated at 37° C. with 5% $CO_2$ for another 6 days.

The supernatant was harvested by addition of cOmplete Mini EDTA-free Protease Inhibitor Cocktail (Roche), centrifuged at 1,000 g for 3 min, and filtered through a 0.45 µm syringe filter to remove cell debris. 2.5% of 10×Ni-NTA or 10×TP buffer was added for pH adjustment.

EpCAM-SpyTag was purified from HEK293T cells by mixing 50 mL of the supernatant with 0.5 mL packed SpyDock resin (also known as Spy&Go resin, described above) and rolling for 1 h at 4° C. The mixture was then purified by standard gravity column chromatography, washing 4× with 20 resin volumes of Tris-phosphate buffer and eluting with 6×1 resin volume of elution buffer.

Figure 4:
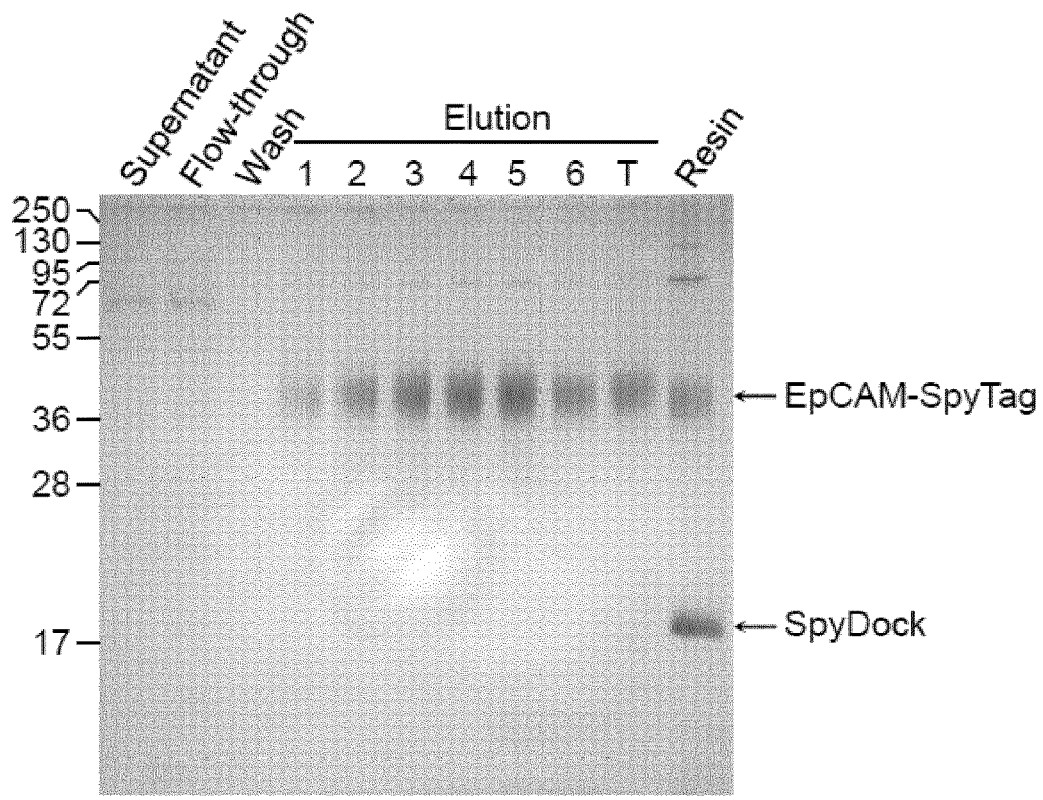
Figure 4:
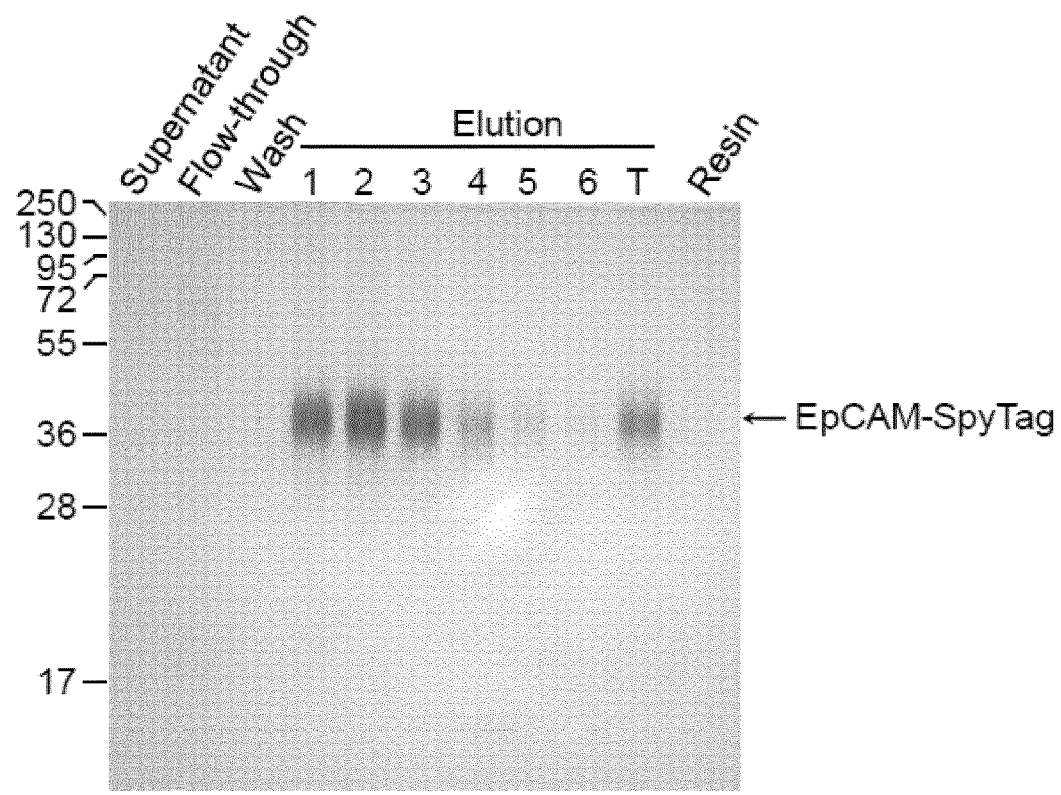

After expression, the same volume of supernatant from the cell culture was incubated with SpyDock resin or Ni-NTA resin and purified. EpCAM-SpyTag was efficiently purified using both Spy&Go and Ni-NTA (FIG. 4).

Example 5—"Pseudo"-SpyCatcher Variants

In addition to the alanine and aspartic acid mutations described in Example 1, several other proposed unreactive "pseudo"-SpyCatcher mutants were constructed based on the SpyDock sequence (SEQ ID NO: 6), comprising different amino acids at position 79. These mutations included aspartic acid (SEQ ID NO: 23), glycine (SEQ ID NO: 14), asparagine (SEQ ID NO: 15), glutamine (SEQ ID NO: 16), serine (SEQ ID NO: 17), threonine (SEQ ID NO: 18), valine (SEQ ID NO: 19), and a dual mutant in which the both reactive residues in the SpyCatcher002 polypeptide (glutamine at position 79 and lysine at position 30) were substituted with alanine (SEQ ID NO: 20). Different versions of the SpyCatcher polypeptide were also produced in which the reactive glutamate was substituted with alanine (i.e. residue 79 of SEQ ID NO: 10 was mutated to alanine to produce SEQ ID NO: 21 and residue 79 of SEQ ID NO: 11 was mutated to alanine to produce SEQ ID NO: 22). An N-terminal truncation of SEQ ID NO: 6 was generated to produce SEQ ID NO: 7.

The substitutions in SEQ ID NOs: 14-19 and 23 were selected on the basis that amino acids giving the most negative free energy values for folding energy may provide the best binding stability with SpyTag. Based on Gibbs free energy and total energy calculation using Rosetta software, the ranking would be Q, A, S, N, D, T, G, V, with Q expected to provide the most stable binding and V expected to provide less stable binding. At this site, C was discarded to avoid complication with the resin attachment site and P was discarded to avoid the complication of cis/trans isomerization. These variants were tested both for their reactivity with SpyTag-MBP in solution and for their ability to successfully purify SpyTag-MBP when bound to resin.

Figure 5:
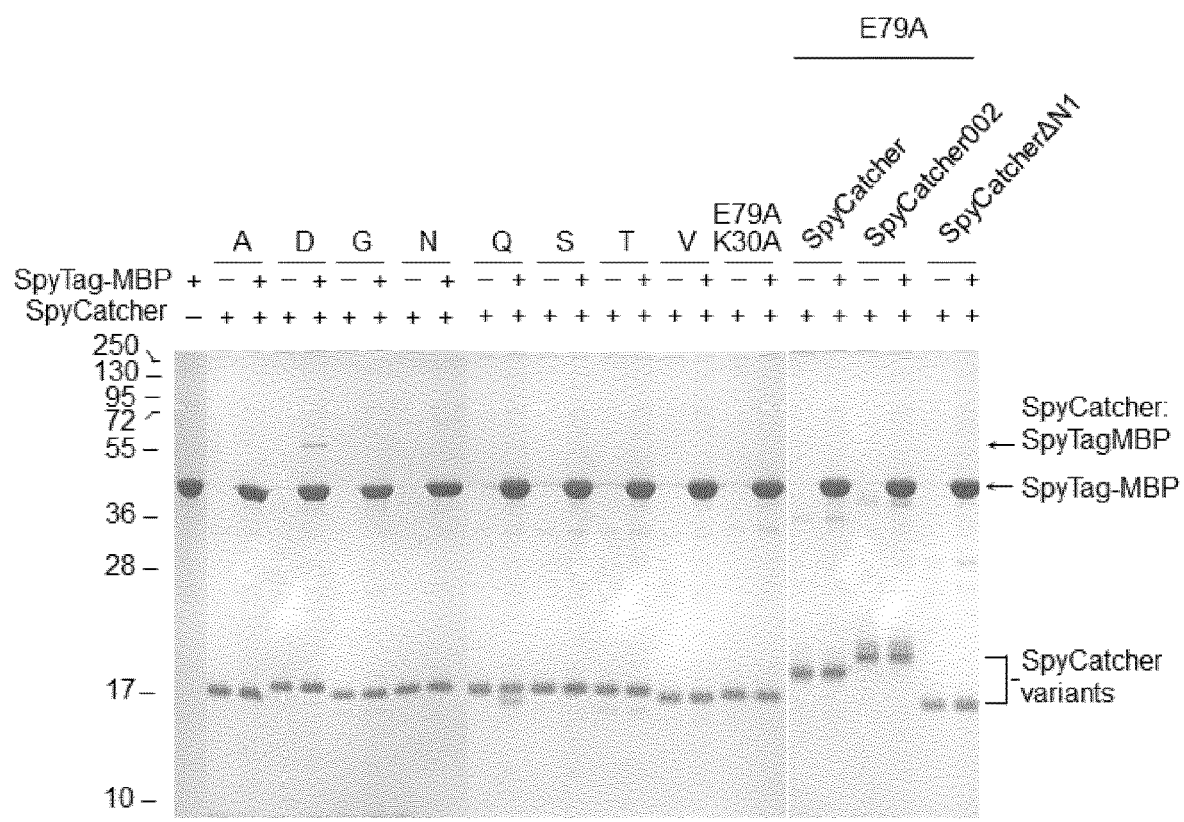

The "pseudo"-SpyCatcher variants were first reacted with SpyTag-MBP in solution in a 1:2 ratio. 5 µM of each variant was incubated with 10 µM SpyTag-MBP at 25° C. for 24 hr in Tris-phosphate buffer (25 mM orthophosphoric acid adjusted to pH 7.0 with Tris base). The results of this experiment are shown in FIG. 5. With the exception of SEQ ID NO: 23, the mutants showed no detectable reaction with SpyTag-MBP.

The same variants were then coupled to resin as described above using the S51C mutation. Pure SpyTag-MBP (0.09 mg) was mixed with 50 µL of each variant resin in 500 µL of Tris-phosphate (25 mM orthophosphoric acid adjusted to pH 7.0 with Tris base) buffer for 1 hr tumbling at 4° C.

The resin was then washed with 4×500 µL wash buffer (500 mM imidazole in Tris-phosphate buffer pH 7.0), before SpyTag-MBP was eluted with 4×75 µL elution buffer (2.5 M imidazole in Tris-phosphate buffer pH 7.0).

Figure 6:
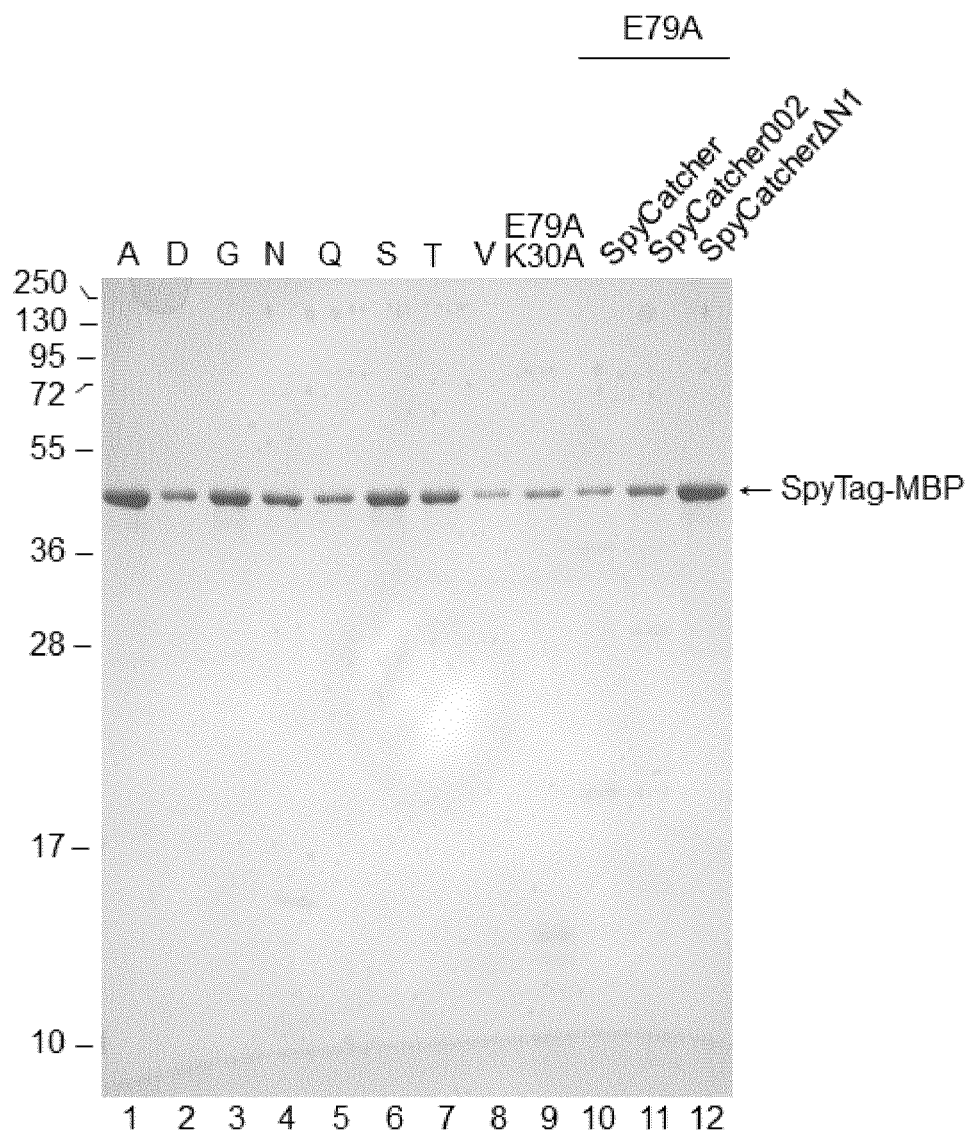

The elution fractions were pooled and loaded onto SDS-PAGE. The results of this experiment are provided in FIG. 6. Surprisingly, and contrary to the expectations based on the Gibbs free energy ranking mentioned above, it was observed that the E79A mutation resulted in elution of the greatest amount of SpyTag-MBP, followed by glycine or serine (about equal), and then asparagine or theonine (about equal), based on the intensity of the band. The results demonstrate that the ΔN1 mutation did not affect the binding and elutability of SpyTag-MBP. Moreover, the additional mutations relative to the SpyCatcher and SpyCatcher002 polypeptides described in Example 1 result in improved purification relative to the parent sequences.

Example 6—Competitive Peptide Elution

SpyTag2.1 (SEQ ID NO: 5), the latest generation of the SpyTag/SpyCatcher technology with the highest binding affinity to all SpyCatcher generations, was used as a competitive elution peptide for Spy&Go, to competitively bind and displace a target protein (MBP) tagged with either SpyTag (SEQ ID NO: 4), SpyTag002 (SEQ ID NO: 3), or SpyTag2.1 (SEQ ID NO: 5).

MBP was fused with each of the three SpyTag peptides, which were then spiked into clarified *E. coli* lysate, washed with 500 mM imidazole in Tris-phosphate pH 7.0 to remove non-specifically bound cellular material, and eluted by incubating with 1 mM SpyTag2.1 peptide dissolved in Tris-phosphate at pH 7.0 at 30° C. for 2 hours. The elution step was then repeated a second time.

Peptide elution using SpyTag2.1 as the competitive peptide resulted in elution of SpyTag-, SpyTag002-, and SpyTag2.1-MBP from the Spy&Go resin (FIG. 9). The elution was still incomplete after 4 hours of incubation at an elevated temperature, as can be seen from the remaining target protein bound in the boiled resin fraction. As expected, more protein was displaced when fused with the first-generation SpyTag compared to the latest generation due to the stronger binding interactions between SpyTag2.1 and SpyDock.

Example 7—Elution by On-Resin Tag Cleavage

To demonstrate on-resin cleavage of SpyTag-protein bound to SpyDock, a TEV recognition site consisting of ENLYFQIG (SEQ ID NO: 26), where I denotes the cleavage site, was inserted downstream of SpyTag and preceding MBP in a SpyTag-MBP construct.

The SpyTag-MBP fusion protein was expressed in *E. coli*, the cells were sonicated to cause lysis, and incubated with Spy&Go resin to allow binding to SpyDock. Non-specific cellular material was then washed with 500 mM imidazole in Tris-phosphate at pH 7.0, and 0.5 mg/mL of polyhistidine tagged SuperTEV fused to MBP was added to the resin to incubate at different time points (2, 4, 20 or 24 hours) at 4° C. Elution of tag-cleaved MBP was already apparent after only 2 hours (FIG. 10). The reaction was optimal after overnight incubation to allow for higher yield.

Example 8—Buffer Compatibility of Spy&go Resin

The buffer-compatibility of Spy&Go resin (described in Example 2) was investigated by spiking purified SpyTag-MBP into different biologically-relevant buffers, binding with Spy&Go resin and attempting to purify the protein following the same wash and elution protocol as above. The buffers that were used included physiological buffers such as PBS and saline Tris-HCl (50 mM Tris-HCl, 300 mM NaCl at pH 7.8), detergents such as Tween 20 (polysorbate 20) and Triton X-100, and denaturants such as urea and guanidine hydrochloride (GuHCl). The detergents were dissolved in Tris-phosphate buffer at pH 7.0, whereas urea was dissolved in 50 mM Tris-HCl at pH 8.0 and GuHCl was dissolved in distilled water at pH 2.0.

The binding and elution of spiked SpyTag-MBP from these buffers were compared to the Tris-phosphate pH 7.0 buffer described above. The efficiency of binding was compared by loading the final pooled elution fractions onto a non-reducing SDS-PAGE gel, as the similar wash and elution conditions should minimise variability between the samples, and the amount of protein eluted should only be affected by binding to Spy&Go resin. Between the three physiological buffers (Tris-phosphate, PBS and saline Tris-HCl), only saline Tris-HCl impaired the binding of SpyTag-MBP to Spy&Go resin (FIG. 11). It was found that Spy&Go was compatible with up to 2% of Tween 20 and Triton X-100, which is comparable to other established affinity purification method such as Ni-NTA for polyhistidine tags and Strep-Tactin for Strep-tag (Qiagen, IBA Lifesciences). For denaturing conditions, the maximum allowable concentration of urea was 2 M, whereas for GuHCl it was 0.5 M without any loss in binding capacity (FIG. 11).

Example 9—Long Term Storage of Spy&go Resin

A common storage buffer for resins is 20% ethanol, as this is sufficiently high to prevent bacterial growth, so as to avoid proteolysing proteins, but is also sufficiently low, so as not to destabilise protein structure or cause precipitation of proteins. Ethanol is also inexpensive, non-toxic and easily disposed of. It was therefore investigated whether Spy&Go resin can tolerate long-term storage in 20% ethanol.

Spy&Go resin was stored in 20% ethanol and its function to purify SpyTag-MBP from lysate was determined and compared with resin before storage. The resin was still functional after 10 months of storage in 20% ethanol at 4° C. (FIG. 12).

Example 10—Regeneration and Reusability of Spy&go Resin

The regeneration and reusability of Spy&Go resin was investigated following interaction between SpyDock and SpyTag-MBP. Initial trials found it difficult to remove residual bound SpyTag-MBP after elution. Isolated attempts at regeneration of Spy&Go resin using either glycine at pH 2, 4 M imidazole at pH 7.0, 6 M GuHCl at pH 6.5, or 0.1 M NaOH did not fully remove the bound SpyTag-MBP. Subsequently, it was found that subjecting the resin with consecutive washes of 4 M imidazole in Tris-phosphate at pH 7.0, 6 M GuHCl at pH 2.0 and 0.1 M NaOH with a physiological wash in between each harsh condition was sufficient to remove the remaining SpyTag-MBP from the used Spy&Go resin to a non-detectable amount on Coomassie-stained SDS-PAGE (FIG. 13A).

The regenerated resin was then compared with a new unused resin to purify another protein, αDR5-SpyTag, which has a different molecular weight than SpyTag-MBP (16 kDa versus 45 kDa). The purity and amount of αDR5-SpyTag purified between the two resins were comparable and the regenerated resin did not have apparent carryover of the bigger SpyTag-MBP from a previous purification (FIG. 13B). From the regeneration regimen, 4 M imidazole and 6 M GuHCl at pH 2.0 served to remove any remaining bound SpyTag-proteins and other contaminating proteins by interaction destabilisation and unfolding of SpyDock.

Methods

Ni-NTA Purification

Ni-NTA purifications were done at 4° C. throughout. All *E. coli*-grown constructs were resuspended in 1×Ni-NTA buffer (50 mM Tris-HCl, 300 mM NaCl pH 7.8) with cOmplete Mini EDTA-free Protease Inhibitor Cocktail and 1 mM phenylmethylsulfonyl fluoride (PMSF). For SpyDock, 10 mM 2-mercaptoethanol was also added. Cells were lysed by addition of 100 μg/mL lysozyme (Sigma-Aldrich) and 2 U/mL benzonase (Sigma-Aldrich), rotated at 25° C. for 30 min, and subsequently sonicated on ice for 4×1 min with 1 min rest period at 50% duty cycle. Clarified cell lysates were centrifuged at 30,000 g for 30 min before incubation with Ni-NTA resin (Qiagen) on a rotary shaker for 1 h. The lysate-bead mixture was added onto a Polyprep gravity column and washed with 20 packed resin volumes of Ni-NTA wash buffer (10 mM imidazole in Ni-NTA buffer, pH 7.8). 10 mM 2-mercaptoethanol was included for the first 10 packed resin volumes with SpyDock. Proteins were eluted with Ni-NTA elution buffer (200 mM imidazole in Ni-NTA buffer, pH 7.8). Elution was monitored by A280 and stopped once A280<1.0. Proteins were dialyzed against 20 mM Tris-HCl pH 8.0 and concentrated, if necessary, using Vivaspin centrifugal concentrator 5 kDa cutoff (GE Healthcare).

SpyDock was further purified on a HiTrap Q HP anion-exchange chromatography column (GE Healthcare) connected to an ÄKTA Pure 25 (GE Healthcare) fast protein liquid chromatography (FPLC) system at 4° C. The protein was eluted with a linear gradient of 0.2-0.35 M NaCl (in 10 mM Tris-HCl pH 8.0 with 1 mM dithiothreitol) at a flow rate of 2 mL/min at 4° C. Peak fractions were verified by SDS-PAGE, dialyzed against 20 mM Tris-HCl pH 8.0, and concentrated using a Vivaspin centrifugal concentrator 5 kDa cutoff.

SDS-PAGE and Protein Purity Quantification.

SDS-PAGE was performed using 16% Tris-glycine gels in an XCell SureLock system (Thermo Fisher Scientific). Samples were loaded with final concentration of 1×SDS-PAGE loading buffer. For reduced samples, 100 mM 2-mercaptoethanol was added. SDS-PAGE was run at 200 V in 25 mM Tris-HCl, 192 mM glycine, 0.1% (w/v) SDS, pH 8.5. Gels were stained with InstantBlue Coomassie stain (Expedeon), destained with MilliQ water, and imaged using ChemiDoc XRS imager with ImageLab (version 5.2) (Bio-Rad). In ImageLab, low sensitivity band detection in the final eluted lane (T) was calculated and compared with the protein control lane (Protein) at background subtraction of disk size 2 mm. Percentage purity is defined as 100×[target protein Band % in lane T/target protein Band % in lane Protein].

The invention claimed is:

1. A polypeptide comprising:
   (i) an amino acid sequence as set forth in SEQ ID NO: 1, wherein X at position 79 is selected from alanine, glycine, serine, asparagine, or threonine;
   (ii) a portion of (i) comprising an amino acid sequence as set forth in SEQ ID NO: 2, wherein X at position 56 is selected from alanine, glycine, serine, asparagine or threonine;
   (iii) an amino acid sequence with at least 85% sequence identity to a sequence as set forth in SEQ ID NO: 1, wherein the polypeptide comprises alanine, glycine, serine, asparagine or threonine at a position equivalent to position 79 of SEQ ID NO: 1; or
   (iv) a portion of (iii) comprising an amino acid sequence with at least 80% sequence identity to a sequence as set forth in SEQ ID NO: 2, wherein the polypeptide comprises alanine, glycine, serine, asparagine or threonine at a position equivalent to position 56 of SEQ ID NO: 2, wherein the polypeptide binds selectively and reversibly to a cognate peptide comprising an amino acid sequence as set forth in SEQ ID NO: 3, 4 or 5.

2. The polypeptide of claim 1, wherein X at a position equivalent to position 79 of SEQ ID NO: 1 or position 56 of SEQ ID NO: 2 is selected from alanine, glycine or serine.

3. The polypeptide of claim 1, wherein X at a position equivalent to position 79 of SEQ ID NO: 1 or position 56 of SEQ ID NO: 2 is alanine.

4. The polypeptide of claim 1, wherein the polypeptide comprises the amino acid sequence with at least 85% sequence identity to a sequence as set forth in SEQ ID NO: 1 and wherein the amino acid sequence comprises one or more of the following:
  (1) lysine at a position equivalent to position 33 of SEQ ID NO: 1;
  (2) proline at a position equivalent to position 91 of SEQ ID NO: 1;
  (3) aspartic acid at a position equivalent to position 99 of SEQ ID NO: 1; and
  (4) glutamic acid at a position equivalent to position 110 of SEQ ID NO: 1.

5. The polypeptide of claim 1, wherein the polypeptide comprises the amino acid sequence with at least 85% sequence identity to a sequence as set forth in SEQ ID NO: 1, wherein the amino acid sequence comprises lysine at position 33, proline at position 91, aspartic acid at position 99, glutamic acid at position 110 and one or more of the following:
  i) threonine at position 4;
  ii) glycine at position 11;
  iii) proline at position 15;
  iv) threonine at position 21;
  v) arginine at position 39;
  vi) histidine at position 64;
  vii) glutamic acid at position 107; and
  viii) threonine at position 115,
  wherein the specified amino acid residues are at positions equivalent to the positions in SEQ ID NO: 1.

6. The polypeptide of claim 1, wherein the polypeptide comprises the amino acid sequence with at least 85% sequence identity to a sequence as set forth in SEQ ID NO: 1 and wherein the amino acid sequence comprises:
  i) threonine at position 4;
  ii) glycine at position 11;
  iii) proline at position 15;
  iv) threonine at position 21;
  v) lysine at position 33;
  vi) arginine at position 39;
  vii) histidine at position 64;
  viii) proline at position 91;
  ix) aspartic acid at position 99;
  x) glutamic acid at position 107;
  xi) glutamic acid at position 110; and
  xii) threonine at position 115,
  wherein the specified amino acid residues are at positions equivalent to the positions in SEQ ID NO: 1.

7. The polypeptide of claim 1, wherein the polypeptide comprises the amino acid sequence with at least 85% sequence identity to a sequence as set forth in SEQ ID NO: 1 and wherein the amino acid sequence comprises cysteine at a position equivalent to position 51 in SEQ ID NO: 1 or position 28 in SEQ ID NO: 2.

8. The polypeptide of claim 1, wherein the polypeptide is immobilized on a solid substrate.

9. The polypeptide of claim 8, wherein the polypeptide is immobilized on the solid substrate via a covalent bond.

10. The polypeptide of claim 8, wherein the polypeptide comprises the amino acid sequence with at least 85% sequence identity to a sequence as set forth in SEQ ID NO: 1 and wherein the amino acid sequence comprises cysteine at position 51 and the polypeptide is immobilized on the solid substrate via a covalent bond between said cysteine and the solid substrate, wherein the specified amino acid residue is at a position equivalent to the position in SEQ ID NO: 1.

11. A kit for use in preparing a solid substrate on which a polypeptide as defined in claim 1 is immobilized, comprising:
  a) the polypeptide as defined in claim 1; and
  b) means for immobilizing the polypeptide of a) on a solid substrate,
  wherein the means for immobilizing comprise:
  (i) reagents for activating the solid substrate and/or polypeptide;
  (ii) reagents for coupling the polypeptide to the solid substrate; and/or
  iii) reagents for blocking the solid substrate.

12. The kit of claim 11 further comprising the solid substrate.

* * * * *

SEQUENCE LISTING

<160> NUMBER OF SEQ ID NOS: 26

<210> SEQ ID NO 1
<211> LENGTH: 115
<212> TYPE: PRT
<213> ORGANISM: Artificial Sequence
<220> FEATURE:
<223> OTHER INFORMATION: SpyDock variant
<220> FEATURE:
<221> NAME/KEY: MISC_FEATURE
<222> LOCATION: (79)..(79)
<223> OTHER INFORMATION: X is alanine, glycine, serine, asparagine or threonine

<400> SEQUENCE: 1

Ala Met Val Thr Thr Leu Ser Gly Leu Ser Gly Glu Gln Gly Pro Ser
1               5                   10                  15

Gly Asp Met Thr Thr Glu Glu Asp Ser Ala Thr His Ile Lys Phe Ser
            20                  25                  30

Lys Arg Asp Glu Asp Gly Arg Glu Leu Ala Gly Ala Thr Met Glu Leu
        35                  40                  45

Arg Asp Cys Ser Gly Lys Thr Ile Ser Thr Trp Ile Ser Asp Gly His
50                  55                  60

Val Lys Asp Phe Tyr Leu Tyr Pro Gly Lys Tyr Thr Phe Val Xaa Thr
65                  70                  75                  80

Ala Ala Pro Asp Gly Tyr Glu Val Ala Thr Pro Ile Thr Phe Thr Val
                85                  90                  95

Asn Glu Asp Gly Gln Val Thr Val Asn Gly Glu Ala Thr Glu Gly Asp
            100                 105                 110

Ala His Thr
        115

<210> SEQ ID NO 2
<211> LENGTH: 92
<212> TYPE: PRT
<213> ORGANISM: Artificial Sequence
<220> FEATURE:
<223> OTHER INFORMATION: Portion of SpyDock variant
<220> FEATURE:
<221> NAME/KEY: MISC_FEATURE
<222> LOCATION: (56)..(56)
<223> OTHER INFORMATION: X is alanine, glycine, serine, asparagine or threonine

<400> SEQUENCE: 2

Asp Ser Ala Thr His Ile Lys Phe Ser Lys Arg Asp Glu Asp Gly Arg
1               5                   10                  15

Glu Leu Ala Gly Ala Thr Met Glu Leu Arg Asp Cys Ser Gly Lys Thr
            20                  25                  30

Ile Ser Thr Trp Ile Ser Asp Gly His Val Lys Asp Phe Tyr Leu Tyr
        35                  40                  45

Pro Gly Lys Tyr Thr Phe Val Xaa Thr Ala Ala Pro Asp Gly Tyr Glu
    50                  55                  60

Val Ala Thr Pro Ile Thr Phe Thr Val Asn Glu Asp Gly Gln Val Thr
65                  70                  75                  80

Val Asn Gly Glu Ala Thr Glu Gly Asp Ala His Thr
            85                  90

<210> SEQ ID NO 3
<211> LENGTH: 14
<212> TYPE: PRT
<213> ORGANISM: Artificial Sequence

```
<220> FEATURE:
<223> OTHER INFORMATION: SpyTag 002

<400> SEQUENCE: 3

Val Pro Thr Ile Val Met Val Asp Ala Tyr Lys Arg Tyr Lys
1               5                   10

<210> SEQ ID NO 4
<211> LENGTH: 13
<212> TYPE: PRT
<213> ORGANISM: Artificial Sequence
<220> FEATURE:
<223> OTHER INFORMATION: SpyTag

<400> SEQUENCE: 4

Ala His Ile Val Met Val Asp Ala Tyr Lys Pro Thr Lys
1               5                   10

<210> SEQ ID NO 5
<211> LENGTH: 16
<212> TYPE: PRT
<213> ORGANISM: Artificial Sequence
<220> FEATURE:
<223> OTHER INFORMATION: SpyTag2.1

<400> SEQUENCE: 5

Arg Gly Val Pro His Ile Val Met Val Asp Ala Tyr Lys Arg Tyr Lys
1               5                   10                  15

<210> SEQ ID NO 6
<211> LENGTH: 115
<212> TYPE: PRT
<213> ORGANISM: Artificial Sequence
<220> FEATURE:
<223> OTHER INFORMATION: SpyDock

<400> SEQUENCE: 6

Ala Met Val Thr Thr Leu Ser Gly Leu Ser Gly Glu Gln Gly Pro Ser
1               5                   10                  15

Gly Asp Met Thr Thr Glu Glu Asp Ser Ala Thr His Ile Lys Phe Ser
                20                  25                  30

Lys Arg Asp Glu Asp Gly Arg Glu Leu Ala Gly Ala Thr Met Glu Leu
            35                  40                  45

Arg Asp Cys Ser Gly Lys Thr Ile Ser Thr Trp Ile Ser Asp Gly His
        50                  55                  60

Val Lys Asp Phe Tyr Leu Tyr Pro Gly Lys Tyr Thr Phe Val Ala Thr
65                  70                  75                  80

Ala Ala Pro Asp Gly Tyr Glu Val Ala Thr Pro Ile Thr Phe Thr Val
                85                  90                  95

Asn Glu Asp Gly Gln Val Thr Val Asn Gly Glu Ala Thr Glu Gly Asp
            100                 105                 110

Ala His Thr
        115

<210> SEQ ID NO 7
<211> LENGTH: 92
<212> TYPE: PRT
<213> ORGANISM: Artificial Sequence
<220> FEATURE:
<223> OTHER INFORMATION: Portion of SpyDock

<400> SEQUENCE: 7

Asp Ser Ala Thr His Ile Lys Phe Ser Lys Arg Asp Glu Asp Gly Arg
```

```
              1               5                  10                  15
            Glu Leu Ala Gly Ala Thr Met Glu Leu Arg Asp Cys Ser Gly Lys Thr
                             20                  25                  30

Ile Ser Thr Trp Ile Ser Asp Gly His Val Lys Asp Phe Tyr Leu Tyr
                         35                  40                  45

Pro Gly Lys Tyr Thr Phe Val Ala Thr Ala Ala Pro Asp Gly Tyr Glu
                     50                  55                  60

Val Ala Thr Pro Ile Thr Phe Thr Val Asn Glu Asp Gly Gln Val Thr
             65                  70                  75                  80

Val Asn Gly Glu Ala Thr Glu Gly Asp Ala His Thr
                             85                  90

<210> SEQ ID NO 8
<211> LENGTH: 345
<212> TYPE: DNA
<213> ORGANISM: Artificial Sequence
<220> FEATURE:
<223> OTHER INFORMATION: SpyDock DNA

<400> SEQUENCE: 8
gccatggtaa ccaccttatc aggtttatca ggtgagcaag gtccgtccgg tgatatgaca     60
actgaagaag atagtgctac ccatattaaa ttctcaaaac gtgatgagga cggccgtgag    120
ttagctggtg caactatgga gttgcgtgat tgctctggta aaactattag tacatggatt    180
tcagatggac atgtgaagga tttctacctg tatccaggaa aatatacatt tgtcgcgacc    240
gcagcaccag acggttatga ggtagcaact ccaattacct ttacagttaa tgaggacggt    300
caggttactg taaatggcga agcaactgaa ggtgacgctc atact                    345

<210> SEQ ID NO 9
<211> LENGTH: 276
<212> TYPE: DNA
<213> ORGANISM: Artificial Sequence
<220> FEATURE:
<223> OTHER INFORMATION: Portion of SpyDock DNA

<400> SEQUENCE: 9
gatagtgcta cccatattaa attctcaaaa cgtgatgagg acggccgtga gttagctggt     60
gcaactatgg agttgcgtga ttgctctggt aaaactatta gtacatggat ttcagatgga    120
catgtgaagg atttctacct gtatccagga aaatatacat ttgtcgcgac cgcagcacca    180
gacggttatg aggtagcaac tccaattacc tttacagtta atgaggacgg tcaggttact    240
gtaaatggcg aagcaactga aggtgacgct catact                              276

<210> SEQ ID NO 10
<211> LENGTH: 115
<212> TYPE: PRT
<213> ORGANISM: Artificial Sequence
<220> FEATURE:
<223> OTHER INFORMATION: SpyCatcher

<400> SEQUENCE: 10

Ala Met Val Asp Thr Leu Ser Gly Leu Ser Ser Glu Gln Gly Gln Ser
             1               5                  10                  15

Gly Asp Met Thr Ile Glu Glu Asp Ser Ala Thr His Ile Lys Phe Ser
                             20                  25                  30

Lys Arg Asp Glu Asp Gly Lys Glu Leu Ala Gly Ala Thr Met Glu Leu
                         35                  40                  45

Arg Asp Ser Ser Gly Lys Thr Ile Ser Thr Trp Ile Ser Asp Gly Gln
```

```
Val Lys Asp Phe Tyr Leu Tyr Pro Gly Lys Tyr Thr Phe Val Glu Thr
 65                  70                  75                  80

Ala Ala Pro Asp Gly Tyr Glu Val Ala Thr Ala Ile Thr Phe Thr Val
                 85                  90                  95

Asn Glu Gln Gly Gln Val Thr Val Asn Gly Lys Ala Thr Lys Gly Asp
                100                 105                 110

Ala His Ile
        115
```

<210> SEQ ID NO 11
<211> LENGTH: 115
<212> TYPE: PRT
<213> ORGANISM: Artificial Sequence
<220> FEATURE:
<223> OTHER INFORMATION: SpyCatcher002

<400> SEQUENCE: 11

```
Ala Met Val Thr Thr Leu Ser Gly Leu Ser Gly Glu Gln Gly Pro Ser
  1               5                  10                  15

Gly Asp Met Thr Thr Glu Glu Asp Ser Ala Thr His Ile Lys Phe Ser
                 20                  25                  30

Lys Arg Asp Glu Asp Gly Arg Glu Leu Ala Gly Ala Thr Met Glu Leu
                 35                  40                  45

Arg Asp Ser Ser Gly Lys Thr Ile Ser Thr Trp Ile Ser Asp Gly His
 50                  55                  60

Val Lys Asp Phe Tyr Leu Tyr Pro Gly Lys Tyr Thr Phe Val Glu Thr
 65                  70                  75                  80

Ala Ala Pro Asp Gly Tyr Glu Val Ala Thr Ala Ile Thr Phe Thr Val
                 85                  90                  95

Asn Glu Gln Gly Gln Val Thr Val Asn Gly Glu Ala Thr Lys Gly Asp
                100                 105                 110

Ala His Thr
        115
```

<210> SEQ ID NO 12
<211> LENGTH: 115
<212> TYPE: PRT
<213> ORGANISM: Artificial Sequence
<220> FEATURE:
<223> OTHER INFORMATION: SpyCatcher variant

<400> SEQUENCE: 12

```
Ala Met Val Thr Thr Leu Ser Gly Leu Ser Gly Glu Gln Gly Pro Ser
  1               5                  10                  15

Gly Asp Met Thr Thr Glu Glu Asp Ser Ala Thr His Ile Lys Phe Ser
                 20                  25                  30

Lys Arg Asp Glu Asp Gly Arg Glu Leu Ala Gly Ala Thr Met Glu Leu
                 35                  40                  45

Arg Asp Ser Ser Gly Lys Thr Ile Ser Thr Trp Ile Ser Asp Gly His
 50                  55                  60

Val Lys Asp Phe Tyr Leu Tyr Pro Gly Lys Tyr Thr Phe Val Asp Thr
 65                  70                  75                  80

Ala Ala Pro Asp Gly Tyr Glu Val Ala Thr Pro Ile Thr Phe Thr Val
                 85                  90                  95

Asn Glu Asp Gly Gln Val Thr Val Asn Gly Glu Ala Thr Glu Gly Asp
                100                 105                 110
```

-continued

Ala His Thr
        115

<210> SEQ ID NO 13
<211> LENGTH: 115
<212> TYPE: PRT
<213> ORGANISM: Artificial Sequence
<220> FEATURE:
<223> OTHER INFORMATION: SpyCatcher variant

<400> SEQUENCE: 13

Ala Met Val Thr Thr Leu Ser Gly Leu Ser Gly Glu Gln Gly Pro Ser
1               5                   10                  15

Gly Asp Met Thr Thr Glu Glu Asp Ser Ala Thr His Ile Lys Phe Ser
            20                  25                  30

Lys Arg Asp Glu Asp Gly Arg Glu Leu Ala Gly Ala Thr Met Glu Leu
        35                  40                  45

Arg Asp Ser Ser Gly Lys Thr Ile Ser Thr Trp Ile Ser Asp Gly His
    50                  55                  60

Val Lys Asp Phe Tyr Leu Tyr Pro Gly Lys Tyr Thr Phe Val Ala Thr
65                  70                  75                  80

Ala Ala Pro Asp Gly Tyr Glu Val Ala Thr Pro Ile Thr Phe Thr Val
                85                  90                  95

Asn Glu Asp Gly Gln Val Thr Val Asn Gly Glu Ala Thr Glu Gly Asp
            100                 105                 110

Ala His Thr
        115

<210> SEQ ID NO 14
<211> LENGTH: 115
<212> TYPE: PRT
<213> ORGANISM: Artificial Sequence
<220> FEATURE:
<223> OTHER INFORMATION: SpyCatcher variant

<400> SEQUENCE: 14

Ala Met Val Thr Thr Leu Ser Gly Leu Ser Gly Glu Gln Gly Pro Ser
1               5                   10                  15

Gly Asp Met Thr Thr Glu Glu Asp Ser Ala Thr His Ile Lys Phe Ser
            20                  25                  30

Lys Arg Asp Glu Asp Gly Arg Glu Leu Ala Gly Ala Thr Met Glu Leu
        35                  40                  45

Arg Asp Cys Ser Gly Lys Thr Ile Ser Thr Trp Ile Ser Asp Gly His
    50                  55                  60

Val Lys Asp Phe Tyr Leu Tyr Pro Gly Lys Tyr Thr Phe Val Gly Thr
65                  70                  75                  80

Ala Ala Pro Asp Gly Tyr Glu Val Ala Thr Pro Ile Thr Phe Thr Val
                85                  90                  95

Asn Glu Asp Gly Gln Val Thr Val Asn Gly Glu Ala Thr Glu Gly Asp
            100                 105                 110

Ala His Thr
        115

<210> SEQ ID NO 15
<211> LENGTH: 115
<212> TYPE: PRT
<213> ORGANISM: Artificial Sequence
<220> FEATURE:
<223> OTHER INFORMATION: SpyCatcher variant

<400> SEQUENCE: 15

Ala Met Val Thr Thr Leu Ser Gly Leu Ser Gly Glu Gln Gly Pro Ser
1               5                   10                  15

Gly Asp Met Thr Thr Glu Glu Asp Ser Ala Thr His Ile Lys Phe Ser
            20                  25                  30

Lys Arg Asp Glu Asp Gly Arg Glu Leu Ala Gly Ala Thr Met Glu Leu
        35                  40                  45

Arg Asp Cys Ser Gly Lys Thr Ile Ser Thr Trp Ile Ser Asp Gly His
    50                  55                  60

Val Lys Asp Phe Tyr Leu Tyr Pro Gly Lys Tyr Thr Phe Val Asn Thr
65                  70                  75                  80

Ala Ala Pro Asp Gly Tyr Glu Val Ala Thr Pro Ile Thr Phe Thr Val
                85                  90                  95

Asn Glu Asp Gly Gln Val Thr Val Asn Gly Glu Ala Thr Glu Gly Asp
            100                 105                 110

Ala His Thr
        115

<210> SEQ ID NO 16
<211> LENGTH: 115
<212> TYPE: PRT
<213> ORGANISM: Artificial Sequence
<220> FEATURE:
<223> OTHER INFORMATION: SpyCatcher variant

<400> SEQUENCE: 16

Ala Met Val Thr Thr Leu Ser Gly Leu Ser Gly Glu Gln Gly Pro Ser
1               5                   10                  15

Gly Asp Met Thr Thr Glu Glu Asp Ser Ala Thr His Ile Lys Phe Ser
            20                  25                  30

Lys Arg Asp Glu Asp Gly Arg Glu Leu Ala Gly Ala Thr Met Glu Leu
        35                  40                  45

Arg Asp Cys Ser Gly Lys Thr Ile Ser Thr Trp Ile Ser Asp Gly His
    50                  55                  60

Val Lys Asp Phe Tyr Leu Tyr Pro Gly Lys Tyr Thr Phe Val Gln Thr
65                  70                  75                  80

Ala Ala Pro Asp Gly Tyr Glu Val Ala Thr Pro Ile Thr Phe Thr Val
                85                  90                  95

Asn Glu Asp Gly Gln Val Thr Val Asn Gly Glu Ala Thr Glu Gly Asp
            100                 105                 110

Ala His Thr
        115

<210> SEQ ID NO 17
<211> LENGTH: 115
<212> TYPE: PRT
<213> ORGANISM: Artificial Sequence
<220> FEATURE:
<223> OTHER INFORMATION: SpyCatcher variant

<400> SEQUENCE: 17

Ala Met Val Thr Thr Leu Ser Gly Leu Ser Gly Glu Gln Gly Pro Ser
1               5                   10                  15

Gly Asp Met Thr Thr Glu Glu Asp Ser Ala Thr His Ile Lys Phe Ser
            20                  25                  30

Lys Arg Asp Glu Asp Gly Arg Glu Leu Ala Gly Ala Thr Met Glu Leu
        35                  40                  45

```
Arg Asp Cys Ser Gly Lys Thr Ile Ser Thr Trp Ile Ser Asp Gly His
    50                  55                  60

Val Lys Asp Phe Tyr Leu Tyr Pro Gly Lys Tyr Thr Phe Val Ser Thr
65                  70                  75                  80

Ala Ala Pro Asp Gly Tyr Glu Val Ala Thr Pro Ile Thr Phe Thr Val
                85                  90                  95

Asn Glu Asp Gly Gln Val Thr Val Asn Gly Glu Ala Thr Glu Gly Asp
                100                 105                 110

Ala His Thr
        115

<210> SEQ ID NO 18
<211> LENGTH: 115
<212> TYPE: PRT
<213> ORGANISM: Artificial Sequence
<220> FEATURE:
<223> OTHER INFORMATION: SpyCatcher variant

<400> SEQUENCE: 18

Ala Met Val Thr Thr Leu Ser Gly Leu Ser Gly Glu Gln Gly Pro Ser
1               5                   10                  15

Gly Asp Met Thr Thr Glu Glu Asp Ser Ala Thr His Ile Lys Phe Ser
                20                  25                  30

Lys Arg Asp Glu Asp Gly Arg Glu Leu Ala Gly Ala Thr Met Glu Leu
            35                  40                  45

Arg Asp Cys Ser Gly Lys Thr Ile Ser Thr Trp Ile Ser Asp Gly His
    50                  55                  60

Val Lys Asp Phe Tyr Leu Tyr Pro Gly Lys Tyr Thr Phe Val Thr Thr
65                  70                  75                  80

Ala Ala Pro Asp Gly Tyr Glu Val Ala Thr Pro Ile Thr Phe Thr Val
                85                  90                  95

Asn Glu Asp Gly Gln Val Thr Val Asn Gly Glu Ala Thr Glu Gly Asp
                100                 105                 110

Ala His Thr
        115

<210> SEQ ID NO 19
<211> LENGTH: 115
<212> TYPE: PRT
<213> ORGANISM: Artificial Sequence
<220> FEATURE:
<223> OTHER INFORMATION: SpyCatcher variant

<400> SEQUENCE: 19

Ala Met Val Thr Thr Leu Ser Gly Leu Ser Gly Glu Gln Gly Pro Ser
1               5                   10                  15

Gly Asp Met Thr Thr Glu Glu Asp Ser Ala Thr His Ile Lys Phe Ser
                20                  25                  30

Lys Arg Asp Glu Asp Gly Arg Glu Leu Ala Gly Ala Thr Met Glu Leu
            35                  40                  45

Arg Asp Cys Ser Gly Lys Thr Ile Ser Thr Trp Ile Ser Asp Gly His
    50                  55                  60

Val Lys Asp Phe Tyr Leu Tyr Pro Gly Lys Tyr Thr Phe Val Val Thr
65                  70                  75                  80

Ala Ala Pro Asp Gly Tyr Glu Val Ala Thr Pro Ile Thr Phe Thr Val
                85                  90                  95

Asn Glu Asp Gly Gln Val Thr Val Asn Gly Glu Ala Thr Glu Gly Asp
                100                 105                 110
```

Ala His Thr
        115

<210> SEQ ID NO 20
<211> LENGTH: 115
<212> TYPE: PRT
<213> ORGANISM: Artificial Sequence
<220> FEATURE:
<223> OTHER INFORMATION: SpyCatcher variant

<400> SEQUENCE: 20

Ala Met Val Thr Thr Leu Ser Gly Leu Ser Gly Glu Gln Gly Pro Ser
1               5                   10                  15

Gly Asp Met Thr Thr Glu Glu Asp Ser Ala Thr His Ile Ala Phe Ser
            20                  25                  30

Lys Arg Asp Glu Asp Gly Arg Glu Leu Ala Gly Ala Thr Met Glu Leu
        35                  40                  45

Arg Asp Cys Ser Gly Lys Thr Ile Ser Thr Trp Ile Ser Asp Gly His
    50                  55                  60

Val Lys Asp Phe Tyr Leu Tyr Pro Gly Lys Tyr Thr Phe Val Ala Thr
65                  70                  75                  80

Ala Ala Pro Asp Gly Tyr Glu Val Ala Thr Pro Ile Thr Phe Thr Val
                85                  90                  95

Asn Glu Asp Gly Gln Val Thr Val Asn Gly Glu Ala Thr Glu Gly Asp
            100                 105                 110

Ala His Thr
        115

<210> SEQ ID NO 21
<211> LENGTH: 115
<212> TYPE: PRT
<213> ORGANISM: Artificial Sequence
<220> FEATURE:
<223> OTHER INFORMATION: SpyCatcher variant

<400> SEQUENCE: 21

Ala Met Val Asp Thr Leu Ser Gly Leu Ser Ser Glu Gln Gly Gln Ser
1               5                   10                  15

Gly Asp Met Thr Ile Glu Glu Asp Ser Ala Thr His Ile Lys Phe Ser
            20                  25                  30

Lys Arg Asp Glu Asp Gly Lys Glu Leu Ala Gly Ala Thr Met Glu Leu
        35                  40                  45

Arg Asp Cys Ser Gly Lys Thr Ile Ser Thr Trp Ile Ser Asp Gly Gln
    50                  55                  60

Val Lys Asp Phe Tyr Leu Tyr Pro Gly Lys Tyr Thr Phe Val Ala Thr
65                  70                  75                  80

Ala Ala Pro Asp Gly Tyr Glu Val Ala Thr Ala Ile Thr Phe Thr Val
                85                  90                  95

Asn Glu Gln Gly Gln Val Thr Val Asn Gly Lys Ala Thr Lys Gly Asp
            100                 105                 110

Ala His Ile
        115

<210> SEQ ID NO 22
<211> LENGTH: 115
<212> TYPE: PRT
<213> ORGANISM: Artificial Sequence
<220> FEATURE:
<223> OTHER INFORMATION: SpyCatcher variant

<400> SEQUENCE: 22

Ala Met Val Thr Thr Leu Ser Gly Leu Ser Gly Glu Gln Gly Pro Ser
1               5                   10                  15

Gly Asp Met Thr Thr Glu Glu Asp Ser Ala Thr His Ile Lys Phe Ser
            20                  25                  30

Lys Arg Asp Glu Asp Gly Arg Glu Leu Ala Gly Ala Thr Met Glu Leu
        35                  40                  45

Arg Asp Cys Ser Gly Lys Thr Ile Ser Thr Trp Ile Ser Asp Gly His
    50                  55                  60

Val Lys Asp Phe Tyr Leu Tyr Pro Gly Lys Tyr Thr Phe Val Ala Thr
65                  70                  75                  80

Ala Ala Pro Asp Gly Tyr Glu Val Ala Thr Ala Ile Thr Phe Thr Val
                85                  90                  95

Asn Glu Gln Gly Gln Val Thr Val Asn Gly Glu Ala Thr Lys Gly Asp
            100                 105                 110

Ala His Thr
        115

<210> SEQ ID NO 23
<211> LENGTH: 115
<212> TYPE: PRT
<213> ORGANISM: Artificial Sequence
<220> FEATURE:
<223> OTHER INFORMATION: SpyCatcher variant

<400> SEQUENCE: 23

Ala Met Val Thr Thr Leu Ser Gly Leu Ser Gly Glu Gln Gly Pro Ser
1               5                   10                  15

Gly Asp Met Thr Thr Glu Glu Asp Ser Ala Thr His Ile Lys Phe Ser
            20                  25                  30

Lys Arg Asp Glu Asp Gly Arg Glu Leu Ala Gly Ala Thr Met Glu Leu
        35                  40                  45

Arg Asp Cys Ser Gly Lys Thr Ile Ser Thr Trp Ile Ser Asp Gly His
    50                  55                  60

Val Lys Asp Phe Tyr Leu Tyr Pro Gly Lys Tyr Thr Phe Val Asp Thr
65                  70                  75                  80

Ala Ala Pro Asp Gly Tyr Glu Val Ala Thr Pro Ile Thr Phe Thr Val
                85                  90                  95

Asn Glu Asp Gly Gln Val Thr Val Asn Gly Glu Ala Thr Glu Gly Asp
            100                 105                 110

Ala His Thr
        115

<210> SEQ ID NO 24
<211> LENGTH: 122
<212> TYPE: PRT
<213> ORGANISM: Artificial Sequence
<220> FEATURE:
<223> OTHER INFORMATION: SpyCatcher variant

<400> SEQUENCE: 24

Asp Cys Asp Ile Gly Ser Gly Ala Met Val Thr Thr Leu Ser Gly Leu
1               5                   10                  15

Ser Gly Glu Gln Gly Pro Ser Gly Asp Met Thr Thr Glu Glu Asp Ser
            20                  25                  30

Ala Thr His Ile Lys Phe Ser Lys Arg Asp Glu Asp Gly Arg Glu Leu
        35                  40                  45

```
Ala Gly Ala Thr Met Glu Leu Arg Asp Ser Ser Gly Lys Thr Ile Ser
    50                  55                  60

Thr Trp Ile Ser Asp Gly His Val Lys Asp Phe Tyr Leu Tyr Pro Gly
 65              70                  75                  80

Lys Tyr Thr Phe Val Ala Thr Ala Ala Pro Asp Gly Tyr Glu Val Ala
                 85                  90                  95

Thr Pro Ile Thr Phe Thr Val Asn Glu Asp Gly Gln Val Thr Val Asn
            100                 105                 110

Gly Glu Ala Thr Glu Gly Asp Ala His Thr
             115                 120

<210> SEQ ID NO 25
<211> LENGTH: 115
<212> TYPE: PRT
<213> ORGANISM: Artificial Sequence
<220> FEATURE:
<223> OTHER INFORMATION: SpyCatcher variant

<400> SEQUENCE: 25

Ala Met Val Thr Thr Leu Ser Gly Leu Ser Gly Glu Gln Gly Pro Ser
 1               5                  10                  15

Gly Asp Met Thr Thr Glu Glu Asp Ser Ala Thr His Ile Lys Phe Ser
                 20                  25                  30

Lys Arg Asp Glu Asp Gly Arg Glu Leu Ala Gly Ala Thr Met Glu Leu
             35                  40                  45

Arg Asp Ser Ser Gly Lys Thr Ile Cys Thr Trp Ile Ser Asp Gly His
 50                  55                  60

Val Lys Asp Phe Tyr Leu Tyr Pro Gly Lys Tyr Thr Phe Val Ala Thr
 65                  70                  75                  80

Ala Ala Pro Asp Gly Tyr Glu Val Ala Thr Pro Ile Thr Phe Thr Val
                 85                  90                  95

Asn Glu Asp Gly Gln Val Thr Val Asn Gly Glu Ala Thr Glu Gly Asp
             100                 105                 110

Ala His Thr
        115

<210> SEQ ID NO 26
<211> LENGTH: 7
<212> TYPE: PRT
<213> ORGANISM: Artificial Sequence
<220> FEATURE:
<223> OTHER INFORMATION: TEV recognition site

<400> SEQUENCE: 26

Glu Asn Leu Tyr Phe Gln Gly
 1               5
```